(12) United States Patent
Kubo et al.

(10) Patent No.: US 7,524,981 B2
(45) Date of Patent: Apr. 28, 2009

(54) PHOSPHOLIPID DERIVATIVES AND PROCESS FOR THE PRODUCTION THERE

(75) Inventors: Kazuhiro Kubo, Kanagawa (JP); Chika Itoh, Kanagawa (JP); Syunsuke Ohhashi, Kanagawa (JP); Tohru Yasukohchi, Kanagawa (JP); Yusuke Ohkawa, Kanagawa (JP); Hiroshi Kikuchi, Tokyo (JP); Norio Suzuki, Chiba (JP); Miho Takahashi, Shizuoka (JP); Hitoshi Yamauchi, Tokyo (JP)

(73) Assignees: NOF Corporation, Tokyo (JP); DAIICHI Pharmaceutical Co., Ltd., Tokyo (JP)

( * ) Notice: Subject to any disclaimer, the term of this patent is extended or adjusted under 35 U.S.C. 154(b) by 212 days.

(21) Appl. No.: 10/541,309

(22) PCT Filed: Dec. 12, 2003

(86) PCT No.: PCT/JP03/15969

§ 371 (c)(1),
(2), (4) Date: Apr. 13, 2006

(87) PCT Pub. No.: WO2004/060899

PCT Pub. Date: Jul. 22, 2004

(65) Prior Publication Data

US 2006/0210618 A1    Sep. 21, 2006

(30) Foreign Application Priority Data

Jan. 6, 2003    (JP) .............................. 2003-000330

(51) Int. Cl.
C07C 9/02    (2006.01)
(52) U.S. Cl. ...................... 554/78; 554/82; 424/450; 514/114
(58) Field of Classification Search .................. None
See application file for complete search history.

(56) References Cited

U.S. PATENT DOCUMENTS

| | | | |
|---|---|---|---|
| 5,142,036 A | 8/1992 | Akimoto et al. | |
| 5,173,219 A | 12/1992 | Kim | |
| 5,395,619 A | 3/1995 | Zalipsky et al. | |
| 5,540,935 A | 7/1996 | Miyazaki et al. | |
| 5,631,018 A | 5/1997 | Zalipsky et al. | |
| 6,344,576 B1 | 2/2002 | Eibl | |
| 6,436,905 B1 | 8/2002 | Tonge et al. | |
| 2003/0144247 A1 | 7/2003 | Kuwano et al. | |
| 2005/0220856 A1 | 10/2005 | Itoh et al. | |
| 2006/0110436 A1 | 5/2006 | Ohhashi et al. | |
| 2007/0031481 A1 | 2/2007 | Itoh et al. | |

FOREIGN PATENT DOCUMENTS

| | | |
|---|---|---|
| EP | 0373621 | 6/1990 |
| EP | 0657463 | 6/1995 |
| EP | 1279406 | 1/2003 |
| JP | 63-221837 | 9/1988 |
| JP | 2-163108 | 6/1990 |
| JP | 6-228012 | 8/1994 |
| JP | 7-242680 | 9/1995 |
| JP | 7-268038 | 10/1995 |
| JP | 9-255740 | 9/1997 |
| JP | 2002-522442 | 7/2002 |
| WO | 99/09955 | 3/1999 |
| WO | 00/08031 | 2/2000 |
| WO | 00/33817 | 6/2000 |
| WO | 01/05375 | 1/2001 |
| WO | 01/74400 | 10/2001 |
| WO | 03/082882 | 10/2003 |
| WO | 2004/029104 | 4/2004 |
| WO | 2004/083219 | 9/2004 |

OTHER PUBLICATIONS

English language abstract of JP 63-221837, published Sep. 14, 1988.
English language abstract of JP 2-163108, published Jun. 22, 1990.
English language abstract of JP 6-228012, published Aug. 16, 1994.
English language abstract of JP 7-242680, published Sep. 19, 1995.
English language abstract of JP 7-268038, published Oct. 17, 1995.

(Continued)

*Primary Examiner*—Deborah D Carr
(74) *Attorney, Agent, or Firm*—Greenblum & Bernstein, P.L.C.

(57) ABSTRACT

A phospholipid derivative represented by the following formula (1):

$$\left[\left(O\underset{b}{\overset{O}{\overset{\|}{C}}}(CH_2)_a CNHCH_2CH_2O\overset{O}{\overset{\|}{P}}OCH_2\right)\underset{\substack{|\\OM}}{\overset{\substack{H_2C-O\overset{O}{\overset{\|}{C}}-R^1\\|\\CH-O\overset{O}{\overset{\|}{C}}-R^2}}{}}\right]_{k1}$$

$$\left[PG\left(O\underset{b}{\overset{O}{\overset{\|}{C}}}(CH_2)_a\overset{O}{\overset{\|}{C}}OM\right)_{k2}\right]_k$$

$$\left[OH\right]_{k3}$$

wherein [PG]k represents a residue of polyglycerin having a polymerization degree of k, wherein k is 2 to 50, $R^1CO$ and $R^2CO$ independently represent an acyl group having 8 to 22 carbon atoms, symbol "a" independently represents an integer of 0 to 5, symbol "b" independently represents 0 or 1, M represents hydrogen atom, an alkali metal atom, an ammonium, or an organic ammonium, and k1, k2, and k3 represent numbers satisfying the following conditions: $1 \leq k1 \leq (k+2)/2$, $0 \leq k2$, and $k1+k2+k3 = k+2$. The phospholipid derivative is highly safe for living bodies and can be suitably utilized in drug delivery systems such as liposome, and the like.

19 Claims, No Drawings

OTHER PUBLICATIONS

English language abstract of JP 9-255740, published Sep. 30, 1997.

English language abstract of JP 2002-522442, published Jul. 23, 2002.

Harish M. Patel et al., "Inhibitory Effect on Cholesterol on the Uptake of Liposomes by Liver and Spleen", Biochimica et Biophysica Acta, vol. 761, pp. 142-151 (1983).

Carsten F. Gotfredsen et al., "Disposition of Intact Liposomes of Different Compositions and of Liposomal Degradation Products", Biochemical Pharmacology, vol. 32, No. 22. pp. 3381-3387 (1983).

Pharmaceutical Society of Japan, 106th Annula Meeting, Summaries of Symposia, pp. 336 (1986).

T.M. Allen et al., "Large Unilamellar Liposomes with Low Uptake into the Reticuloendothelial System", FEBS Letter, vol. 223, No. 1, pp. 42-46 (1987).

Alexander L. Klibanov et al., "Amphipathic Polyethyleneglycols Effectively Prolong the Circulation Time of Liposomes", FEBS Letter, vol. 268, No. 1, pp. 235-237 (1990).

Shingo Niimi et al., "Effects of Glucocorticoids on Deoxyribonucleic Acid (DNA) Synthesis Stimulated by Growth Factors in Cultured Rat Skin Fibroblasts", Chem. Pharm. Bul., vol. 38, No. 6, pp. 1633-1638 (1990).

Yong Serk Park et al., "Some Negatively Charge Phospholipid Derivatives Prolong the Liposome Circulation in Vivo", Biochimica et Biophysica Acta, vol. 1108, pp. 257-260 (1992).

Database WPI, Section Ch, Week 199546, Derwent Publications Ltd., London, GB, Class A96, AN1995-355265, XP002354282; accompanied by family member JP 07-242680 A.

T. Yuda et al., Biological and Pharmaceutical Bulletin, vol. 19, No. 10, pp. 1347-1351, 1996.

R. Zeisig et al., Biochimica et Biophysica Acta, vol. 1285, No. 2, pp. 237-245, 1996.

T.M. Allen et al., Biochimica et Biophysica Acta, vol. 1061, No. 1, pp. 56-64, 1991.

PHOSPHOLIPID DERIVATIVES AND PROCESS FOR THE PRODUCTION THERE

TECHNICAL FIELD

The present invention relates to a phospholipid derivative containing polyglycerin and a method for producing the same. The present invention also relates to a surfactant, solubilizer, dispersing agent for cosmetics and lipid membrane structure containing the phospholipid derivative.

BACKGROUND ART

Microparticle drug carriers including liposomal drug as typical examples and polypeptides such as protein drug are known to have poor retention in blood and be easily captured by the reticuloendothelial system (hereinafter abbreviated as "RES") such as liver and spleen when they are intravenously administered. The presence of RES is a serious obstacle when a microparticle drug carrier is utilized as a targeting type preparation, which delivers a medicament to organs other than RES, and as a sustained-release preparation, which allows a medicament retained in blood for a long period of time to control the release of the medicament.

Researches have so far been conducted to impart a microcirculation property to the aforementioned preparations. Some proposals have been made, including, for example, a method of maintaining a high blood concentration by reducing a size of liposomes in view of relative easiness of a control of physicochemical properties of lipid bilayers of liposomes (Biochimica et Biophysica Acta, Vol. 761, p. 142, 1983), a method of utilizing lecithin having a high phase transfer temperature (Biochemical Pharmacology, Vol. 32, p. 3381, 1983), a method of utilizing sphingomyelin instead of lecithin (Biochemical Pharmacology, Vol. 32, p. 3381, 1983), a method of adding cholesterol as a membrane component of liposomes (Biochimica et Biophysica Acta, Vol. 761, p. 142, 1983) and the like. However, by applying the aforementioned method, no work has been known so far that successfully provides a microparticle drug carrier having favorable retention in blood and being hardly taken up by RES.

As another approach for solution, researches have been made for providing a microcirculation property and escapability from RES by modification of membrane surfaces of liposomes with a glycolipid, glycoprotein, amino acid-lipid, polyethylene glycol-lipid or the like. Substances for the modification so far reported include, for example, glycophon (The Pharmaceutical Society of Japan, the 106th Annual Meeting, Summaries of Symposia, p.336, 1986), ganglioside GM1 (FEBS Letters, Vol. 223, p.42, 1987), phosphatidylinositol (FEBS Letters, Vol. 223, p.2, 1987), glycophon and ganglioside GM3 (Japanese Patent Unexamined Publication (Kokai) No. 63-22 1837), polyethylene glycol derivative (FEBS Letters, Vol. 268, p.235, 1990), glucuronic acid derivative (Chemical & Pharmaceutical Bulletin, Vol. 38, p. 1633, 1990), glutamic acid derivative (Biochimica et Biophysica Acta, Vol. 1108, p.257, 1992), polyglycerin phospholipid derivative (Japanese Patent Unexamined Publication No. 6-2280 12), and the like.

As the modification of a polypeptide, introduction of two water-soluble polymer molecules into a polypeptide by using triazine has been reported for a purpose of decreasing the number of binding sites of the polypeptide and thereby increasing a residual amount of active groups such as lysine residues in the polypeptide. Also as for a liposome preparation, introduction of two water-soluble polymer molecules into triazine to increase the molecular weight of the water-soluble polymer, and modification of liposome surfaces by using the resulting polymer is reported. However, when a water-soluble polymer is introduced by using triazine, only two water-soluble polymers can be introduced into the triazine ring. Therefore, it is necessary to add a large amount of a compound, which contains two water-soluble polymers introduced in triazine, to increase the number of the water-soluble polymer chains on liposome surfaces. Further, a compound consisting of two or three polyalkylene glycol chains bonded with one functional group has been reported as a polymer modifier. However, the number of the polymer chains, for which this modification can be applied, is limited to 2 or 3, and the aforementioned compound cannot have more than one functional group, because the ends of the polyalkylene glycol chains, except for one end, are blocked with methyl group or ethyl group. It is expected that the effect of this compound to impart microcirculation property to liposome surfaces is inferior to that of a compound having a hydrophilic group. Furthermore, although phospholipid derivatives containing a polyalkylene oxide group have also been used also as surfactants, no compound has been known so far that is safe for living bodies and can be stably used under a condition of a high salt concentration.

DISCLOSURE OF THE INVENTION

An object of the present invention is to provide a phospholipid derivative that is safe for living bodies and can be suitably used in the fields of solubilization and dispersion of physiologically active substances and the like, drug delivery systems such as liposomes, and cosmetics. The inventors of the present invention conducted various researches to achieve the aforementioned object. As a result, they found that novel phospholipid derivatives containing a polyglycerin represented by the following formula had the desired properties. The present invention was achieved on the basis of these findings.

The present invention thus provides a phospholipid derivative, which is represented by the following formula (1):

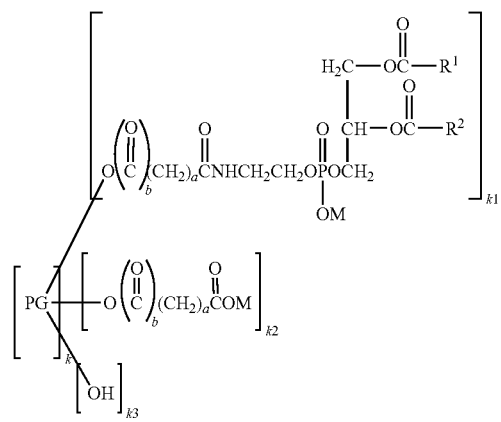

wherein [PG]k represents a residue of polyglycerin having a polymerization degree of k, wherein k is 2 to 50, $R^1CO$ and $R^2CO$ independently represent an acyl group having 8 to 22 carbon atoms, symbol "a" independently represents an integer of 0 to 5, symbol "b" independently represents 0 or 1, M represents hydrogen atom, an alkali metal atom, an ammonium, or an organic ammonium, and k1, k2, and k3 represent numbers satisfying the following conditions: $1 \leq k1 \leq (k+2)/2$, $0 \leq k2$, and $k1+k2+k3=k+2$.

According to preferred embodiments, the present invention provides the aforementioned phospholipid derivative represented by the aforementioned formula (1), wherein k1 satisfies $1 \leq k1 \leq 2$; the aforementioned phospholipid derivative represented by the aforementioned formula (1), wherein k2 satisfies $0 \leq k2 \leq 1$; the aforementioned phospholipid derivative represented by the aforementioned formula (1), wherein k1, k2, and k3 satisfy $8 \leq k1+k2+k3 \leq 52$; the aforementioned phospholipid derivative represented by the aforementioned formula (1), wherein $R^1CO$ and $R^2CO$ independently represent an acyl group having 12 to 20 carbon atoms; the aforementioned phospholipid derivative represented by the aforementioned formula (1), wherein k2 is 0; the aforementioned phospholipid derivative represented by the aforementioned formula (1), wherein a and b represent 0; and the aforementioned phospholipid derivative represented by the aforementioned formula (1), wherein k2 satisfies $0<k2$.

From other aspects, the present invention provides a surfactant comprising the aforementioned phospholipid derivative represented by the aforementioned formula (1); a solubilizer comprising the aforementioned phospholipid derivative represented by the aforementioned formula (1); a dispersing agent, preferably a dispersing agent for cosmetics, comprising the aforementioned phospholipid derivative represented by the aforementioned formula (1); and a lipid membrane structure, preferably a liposome, containing the aforementioned phospholipid derivative represented by the aforementioned formula (1).

From a further aspect, the present invention provides a method for producing the aforementioned phospholipid derivative represented by the aforementioned formula (1), which comprises the step of reacting a compound represented by the following formula (2):

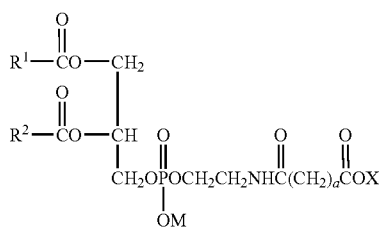

wherein $R^1$, $R^2$, a, and M have the same meanings as those defined above, and X represents hydrogen atom or N-hydroxysuccinimide, and a polyglycerin represented by the following formula (3):

wherein [PG]k represents a residue of polyglycerin having a polymerization degree of k, wherein k has the same meaning as that defined above, and k4 is a number satisfying the following condition: $k4=k+2$. This method can be preferably performed in an organic solvent in the presence of a basic catalyst, more preferably at a temperature within the range of 20 to 90° C. in the presence of a dehydration condensation agent.

The present invention also provides a method for producing a phospholipid derivative represented by the formula (1), which comprises the following steps:

(A) the step of reacting a polyglycerin and a dibasic acid or a halogenated carboxylic acid to obtain a carboxylated polyglycerin; and
(B) the step of reacting the carboxylated polyglycerin obtained in the aforementioned step (A) and a phospholipid, and a method for producing a phospholipid derivative represented by the formula (1), which comprises the following steps:
(A') the step of reacting a polyglycerin and a halogenated carboxylic acid ester and hydrolyzing the obtained ester compound to obtain a carboxylated polyglycerin; and
(B) the step of reacting the carboxylated polyglycerin obtained in the aforementioned step (A) and a phospholipid.

The present invention further provides a method for producing a phospholipid derivative represented by the formula (1), which comprises the step of reacting a polyglycerin derivative represented by the following formula (4):

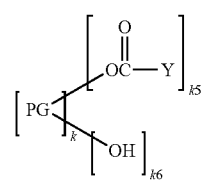

wherein [PG]k represents a residue of polyglyycerin having a polymerization degree of k, wherein k represent a number of 2 to 50, Y represents hydroxyl group or a leaving group, and k5 and k6 are numbers satisfying the following conditions: $1 \leq k5 \leq (k+2)/2$, and $k5+k6=k+2$, and a phospholipid represented by the following formula (5):

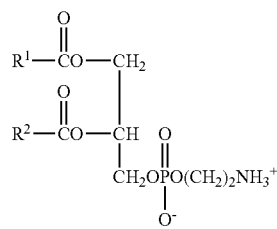

wherein $R^1$ and $R^2$ have the same meanings as those defined above. This method can be preferably performed in an organic solvent in the presence of a basic catalyst, more preferably at a temperature within the range of 20 to 900° C.

From a still further aspect, the present invention provides a pharmaceutical composition comprising a lipid membrane structure (preferably liposome) containing the phospholipid derivative represented by the aforementioned formula (1) and retaining a medicament. The aforementioned pharmaceutical composition wherein the medicament is an antitumor agent is provided as a preferred embodiment.

BEST MODE FOR CARRYING OUT THE INVENTION

In the phospholipid derivative of the present invention represented by the formula (1), [PG]k represents a residue of polyglycerin having a polymerization degree of k, and k1+k2+k3 is k+2. Symbol "k" represents a polymerization degree, and generally means an average polymerization degree. The residue of polyglycerin means a remaining portion of the polyglycerin excluding all of the hydroxyl groups. The polyglycerin constituting the phospholipid derivative represented by the formula (1) is a compound consisting of two or more glycerin molecules linked via ether bonds. For example, when the polyglycerin exists as a linear chain compound, the compound is represented by the formula: HO—$CH_2$—CH(OH)—$CH_2$—[O—$CH_2$—CH(OH)—$CH_2$]$_{k-2}$—O—$CH_2$—CH(OH)—$CH_2$—OH (k is an integer of 2 or more, and means the number of glycerin molecules involved in the polymerization (also sometimes referred to as "polymerization degree")). It can be readily understood by those skilled in the art that the polyglycerin can exist as a branched chain compound. Therefore, the term of polyglycerin used in the specification should not be construed in any limitative way to mean only a linear chain compound. Specific examples of the polyglycerin include diglycerin, triglycerin, tetraglycerin, pentaglycerin, hexaglycerine, heptaglycerin, octaglycerin, nonaglycerin, decaglycerin, didecaglycerin, tridecaglycerin, tetradecaglycerin, and the like. A single substance may be used as the polyglycerin. Alternatively, a mixture of two or more kinds of linear chain and/or branched chain polyglycerin residues having the same or similar polymerization degrees can also be used, and a compound having the residue of polyglycerin such as mentioned above also falls within the scope of the present invention.

Symbol "k1" means the number of residues of the phospholipid compound bonded to the residue of polyglycerin, and the number is 1 to (k+2)/2. When the number of the bonding residues of phospholipid compound k1 is less than 1, the advantageous effects of the present invention cannot be obtained due to smaller numbers of hydrophobic bond portions in a molecule. Further, when the compound of the present invention is used for a lipid membrane structure, k1 preferably satisfies the condition of $1 \leq k1 \leq 2$. When the number of the bonding residues of phospholipid compound satisfies the condition of $2 < k1 \leq (k+2)/2$, namely, when k1 is more than 2, the residues of the phospholipid compound contained in the compound of the present invention increase, in other words, a lot of hydrophobic portions exist in the molecule. Therefore, the compound becomes more likely to form micelles, and thus the compound can be suitably used as a solubilizer or a dispersing agent.

Symbol "k2" represents the number of groups that bond to the residue of polyglycerin of which end is represented by —COOM, and k2 satisfies the condition of $0 \leq k2$. When k2 is 0, it means that any partial structure, of which end is represented by —COOM, does not substantially exist in the compound of the present invention. Further, when k2 is more than 0, carboxyl groups exist and as a result the compound has polarity. Therefore, the compound can be used for a dispersing agent and the like as an ionic surfactant. When k2 satisfies the condition of $0 \leq k2 \leq 1$, the compound does not unstabilize a lipid membrane structure such as liposome, but can stabilize liposomes due to a small number of carboxyl groups, and therefore the compound can be preferably used. M represents hydrogen atom, an alkali metal atom, an ammonium, or an organic ammonium, preferably hydrogen atom or an alkali metal atom. Specific examples include, for example, an alkali metal atom such as sodium and potassium, an organic ammonium such as triethylammonium and diisopropylammonium, and the like.

Symbol "k3" is the number of the hydroxyl groups that bond to the polyglycerin residue, and the number is an integer satisfying the condition of k1+k2+k3=k+2. The value of k1+k2+k3 is an integer of 4 to 52, preferably 8 to 52, more preferably 8 to 12. When the value of k1+k2+k3 is smaller than 4, the advantageous effects of the present invention may not be fully obtained. When the value of k1+k2+k3 is larger than 52, viscosity of the polyglycerin becomes large, and it may become difficult to obtain such a compound.

$R^1CO$ and $R^2CO$ independently represent an acyl group having 8 to 24 carbon atoms, preferably 12 to 20 carbon atoms. The type of the acyl group is not particularly limited, and either an aliphatic acyl group or an aromatic acyl group may be used. However, in general, an acyl group derived from a fatty acid can be preferably used. Specific examples of $R^1CO$ and $R^2CO$ include an acyl group derived from a saturated or unsaturated linear or branched fatty acid such as caprylic acid, capric acid, lauric acid, myristic acid, palmitic acid, palmitoleic acid, stearic acid, isostearic acid, oleic acid, linoleic acid, arachic acid, behenic acid, erucic acid, and lignoceric acid. $R^1CO$ and $R^2CO$ may be the same or different. When the number of carbon atoms exceeds 24, reactivity may sometimes be degraded due to poor dispersion in an aqueous phase. When the number of carbon atoms is less than 8, final purity of the objective substance may sometimes be degraded due to poor crystallizing property during a purification process.

In the formula (1), symbol "b" is independently an integer of 0 or 1. When b is 1, it is preferred that symbol "a" is an integer of 1 to 4, more preferably 2 or 3. When b is 0, it is preferred that a is 0.

Although the method for producing the compound of the present invention represented by the formula (1) is not particularly limited, the compound can be conveniently produced by any of the following methods depending on the structure of the target compound.

<Production Method A>

The phospholipid derivative wherein k2 is 0 can be produced with high purity by, for example, reacting a compound represented by the formula (2) with a compound represented by the formula (3). In the phospholipid compound represented by the formula (2), $R^1$, $R^2$, M, and a are the same as those explained for the formula (1), and X is hydrogen atom or N-hydroxysuccinimide.

The phospholipid compound represented by the formula (2) used as a raw material can be produced by a known method. For example, the compound can be easily produced by reacting a phospholipid compound with a dicarboxylic acid anhydride. The phospholipid to be used may be a natural phospholipid or synthetic phospholipid so long as a phospholipid satisfying the definitions of $R^1$ and $R^2$ is chosen. Examples include, for example, natural and synthetic phosphatidylethanolamines such as soybean phosphatidyldiethanolamine and hydrogenated soybean phosphatidyldiethanolamine, yolk phosphatidyldiethanolamine and hydrogenated yolk phosphatidyldiethanolamine, and the like.

The compound of the present invention represented by the formula (1) can also be produced by reacting an activated ester derivative of a phospholipid compound represented by the formula (2) with a polyglycerin compound represented by the formula (3). The aforementioned activated ester derivative can be obtained by, for example, reacting a phospholipid compound represented by the formula (2) wherein X is hydrogen atom with an activator in the presence of a dehydration condensation agent. The type of the aforementioned activator is not particularly limited, and examples include, for example, N-hydroxysuccinimide, N,N'-disuccinimide carbonate, 1-hydroxybenzotriazole, 4-nitrophenol, N-hydroxy-5-norbornene-2,3-dicarboximide, N-hydroxyphthalimide, 4-hydroxyphenyldimethylsulfonium/methyl sulfate, and the like. Among them, N-hydroxysuccinimide is preferred.

The reaction of the phospholipid compound represented by the formula (2) and the activator can be performed in a solvent that does not react with a carboxylic acid such as chloroform and toluene at a reaction temperature of 15 to 80° C., preferably 25 to 55° C., in the presence of a dehydration condensation agent, and the reaction can be performed by, for example, dispersing the activator in a solution of the phospholipid compound with stirring. For example, when N-hydroxysuccinimide is used as the activator, the carboxyl group of the phospholipid compound represented by the formula (2) and the imide group of N-hydroxysuccinimide will react to produce an activated ester derivative wherein N-hydroxysuccinimide binds to the end of the phospholipid compound represented by the formula (2) on the side of the carboxyl group.

As the organic solvent used for the reaction, those having no reactive functional group such as hydroxyl group can be used without particular limitation. Examples include, for example, ethyl acetate, dichloromethane, chloroform, benzene, toluene, and the like. Among them, chloroform and toluene are preferred. Organic solvents having hydroxyl group such as ethanol may react with the carboxyl group at the end of the polyglycerin compound represented by the formula (4).

The reaction of the phospholipid compound represented by the formula (2) and the polyglycerin compound represented by the formula (3) can be usually performed in an organic solvent in the presence of a basic catalyst, and the reaction can be preferably performed by using a dehydration condensation agent. The type of the basic catalyst is not particularly limited, and examples include, for example, nitrogen-containing substances such as triethylamine, pyridine, dimethylaminopyridine, and ammonium acetate, organic salts such as sodium phosphate, sodium carbonate, sodium hydrogencarbonate, sodium borate, and sodium acetate, and the like. The amount of the basic catalyst may be a minimum amount to complete the reaction, considering the purification step and the like. The basic catalyst is desirably used generally in an amount of 1 to 2 moles, preferably 1 to 1.5 moles, per mole of the phospholipid compound represented by the formula (2), if a reaction rate with the phospholipid compound represented by the formula (2) is taken into consideration. As the organic solvent, those having no reactive functional group such as hydroxyl group can be used without particular limitation. Examples include, for example, ethyl acetate, dichloromethane, chloroform, dimethyl sulfoxide, benzene, toluene, and the like. Among them, dimethyl sulfoxide, chloroform, and toluene are preferred. Organic solvents having hydroxyl group such as ethanol may react with the carboxyl group at the end of the phospholipid compound represented by the formula (2).

When a dehydration condensation agent is used, the type of the dehydration condensation agent is not particularly limited so long as the agent can achieve dehydration condensation of the polyglycerin compound represented by the formula (3) and a functional group of the phospholipid compound represented by the formula (2). Examples of the dehydration condensation agent include, for example, carbodiimide derivatives such as dicyclohexylcarbodiimide and diisopropylcarbodiimide, and dicyclohexylcarbodiimide is especially preferred. The amount of the dehydration condensation agent used is not particularly limited. However, since the polyglycerin compound represented by the formula (3) has many hydroxyl groups, and as a result, has hygroscopic property and contains a lot of moisture. Accordingly, carbodiimide derivatives such as dicyclohexylcarbodiimide and diisopropylcarbodiimide may react with the moisture in the polyglycerin, and thus the objective dehydration condensation reaction of the polyglycerin compound represented by the formula (3) and the functional group of the phospholipid compound represented by the formula (2) may possibly not be completed. Therefore, the amount of the dehydration condensation agent is, for example, preferably about 1 to 10 moles, more preferably about 1 to 5 moles, per mole of the phospholipid compound represented by the formula (2).

By addition of N-hydroxysuccinimide to the reaction system in an amount of 0.1 to 2 moles per mole of the phospholipid compound represented by the formula (2), a reaction rate can be increased.

The amount of the phospholipid compound represented by the formula (2) is not particularly limited. The amount is preferably 1 to 3 moles, more preferably 1 to 1.3 moles based on the number of k1 per one molecule.

The reaction temperature is usually 20 to 90° C., preferably 40 to 80° C. The reaction time is 1 hour or longer, preferably 2 to 8 hours. When the reaction temperature is lower than 20° C., the reaction rate may sometimes be low. When the reaction temperature is higher than 90° C., the acyl group in the phospholipid compound represented by the formula (2) used for the reaction may sometimes be hydrolyzed. In addition, although the compound of the present invention may be obtained as a single compound depending on a synthetic method, the compound may also be obtained as a mixture of substances having different numbers for each of k1, k2, and k3. Such a mixture also falls within the scope of the present invention. Further, the polyglycerin used as a raw material may sometimes not be a single substance, but is a mixture of polyglycerin compounds having two or more kinds of straight and/or branched polyglycerin residues and having the same or similar polymerization degrees. When such material is used, the target substance may be obtained as a mixture of compounds having two or more kinds of structures as for the polyglycerin residue, which mixture also falls within the scope of the present invention. This explanation shall also apply to the reaction steps explained below.

<Production Method B>

The phospholipid derivative of the formula (1) wherein k2 is 0 and the phospholipid derivative of the formula (1) wherein k2 is not 0, i.e., the compound wherein a polyglycerin residue is bonded with a partial structure having carboxyl group at an end, can be produced by reacting a carboxylated polyglycerin with a phospholipid compound according to a method including the aforementioned steps (A) and (B). By reacting the polyglycerin compound with a dibasic acid or a halogenated carboxylic acid in the step (A) to obtain a carboxylated polyglycerin and then reacting the resulting carboxylated polyglycerin with the phospholipid in the step (B), the compound of the present invention can be easily obtained. In the step (A'), by reacting a halogenated carboxylic acid ester instead of the dibasic acid or halogenated carboxylic acid and then performing hydrolyzation, a carboxylated polyglycerin can also be obtained.

Specific examples of the dibasic acid, halogenated carboxylic acid, and halogenated carboxylic acid ester include succinic anhydride, glutaric anhydride, chloropropionic acid, methyl chloropropionate, ethyl chloropropionate, bromopropionic acid, methyl bromopropionate, ethyl bromopropionate, bromohexanoic acid, methyl bromohexanoate, ethyl bromohexanoate, and the like. However, the dibasic acid, halogenated carboxylic acid and halogenated carboxylic acid ester to be reacted with the polyglycerin compound are not limited to the aforementioned compounds, and any compounds may be used so long as a compound successfully provides a carboxylated polyglycerin. The amount of the dibasic acid, halogenated carboxylic acid, or halogenated carboxylic acid ester used in the step (A) or (A') is not particularly limited. The compounds are preferably added in a slightly excessive amount considering a reaction rate. The amount is 1 to 2 moles, preferably 1 to 1.5 moles, based on a desired number of carboxyl groups determined by k2.

As the organic solvent used in the step (A) or (A'), those having no functional group such as hydroxyl group can be used without particular limitation. Examples include, for example, ethyl acetate, dichloromethane, chloroform, dimethyl sulfoxide, benzene, toluene, and the like. Among them, dimethyl sulfoxide, chloroform, and toluene are preferred. Organic solvents having hydroxyl group such as ethanol will react with the dibasic acid, halogenated carboxylic acid and halogenated carboxylic acid ester compound to be reacted with the polyglycerin, and therefore they are not preferred. Although dichloromethane and the like do not have a problem concerning reactivity, they may not be practically preferred due to a low boiling point. A reaction temperature of the step (A) or (') is not particularly limited. The temperature may be, for example, 20 to 110° C., preferably 30 to 90° C. A reaction time is not particularly limited either, and may desirably be, for example, 1 hour or more, preferably 2 to 48 hours. A reaction temperature below 20° C. may not be preferred from a viewpoint of reaction efficiency.

The phospholipid used in the step (B) may be a natural phospholipid or synthetic phospholipid. Examples include, for example, natural and synthetic phosphatidylethanolamines such as soybean phosphatidyldiethanolamine and hydrogenated soybean phosphatidyldiethanolamine, yolk phosphatidyldiethanolamine and hydrogenated yolk phosphatidyldiethanolamine, and the like. As the organic solvent used in the step (B), those having no functional group such as hydroxyl group can be used without particular limitation. Examples include, for example, ethyl acetate, dichloromethane, chloroform, dimethyl sulfoxide, benzene, toluene, and the like. Among them, dimethyl sulfoxide, chloroform, and toluene are preferred. Organic solvents having hydroxyl group such as ethanol will react with the dibasic acid, halogenated carboxylic acid and halogenated carboxylic acid ester compound to be reacted with the polyglycerin, and therefore they are not preferred. Although dichloromethane and the like do not have a problem concerning reactivity, they may not be practically preferred due to a low boiling point. A reaction temperature of the step (B) is not particularly limited, and may be, for example, 20 to 100° C., preferably 20 to 90° C. A reaction time is not particularly limited either, and may desirably be, for example, 0.5 to 24 hours, preferably 1 to 12 hours. A reaction temperature below 20° C. may not be preferred from a viewpoint of reaction efficiency.

For the reaction of the phospholipid compound and carboxylated polyglycerin performed in the step (B), a dehydration condensation agent and/or a basic catalyst can be used. As the dehydration condensation agent, those allowing dehydration condensation of the carboxyl group of the carboxylated polyglycerin and a functional group of the phospholipid compound can be used without particular limitation. Examples of the dehydration condensation agents include, for example, carbodiimide derivatives such as dicyclohexylcarbodiimide. As the dehydration condensation agent, dicyclohexylcarbodiimide is preferred. An amount of the dehydration condensation agent used is desirably about 1 to 5 moles, more preferably about 1 to 2 moles, per mole of the phospholipid compound. Further, it is preferable to add N-hydroxysuccinimide to the reaction system in an amount of 0.1 to 2 moles per mole of the phospholipid compound to increase the reaction efficiency. The type of the basic catalyst used for this reaction is not particularly limited, and examples include, for example, nitrogen-containing substances such as triethylamine, dimethylaminopyridine, and ammonium acetate, organic salts such as sodium phosphate, sodium carbonate, sodium hydrogencarbonate, sodium borate, and sodium acetate, and the like. An amount of the basic catalyst is not particularly limited, and may be, for example, 1 to 5 moles, preferably 1 to 2 moles, per mole of the phospholipid compound used in the step (B). An amount of the phospholipid compound used in the step (B) is not particularly limited, and the compound can be suitably reacted depending on a desired number of k1. For example, the amount is preferably 1 to 3 moles, more preferably 1 to 1.3 moles, based on the number of k1 per one molecule.

<Production Method C>

As for the polyglycerin-modified phospholipid of the present invention, the phospholipid derivative of the formula (1) wherein k2 is 0, and the phospholipid derivative of the formula (1) wherein a and b are 0 can be easily synthesized by reacting a polyglycerin compound represented by the formula (4) with a phospholipid represented by the formula (5). In the polyglycerin compound represented by the formula (4), [PG]k represents a residue of polyglycerin having a polymerization degree of k, wherein k represent a number of 2 to 50, Y represents hydroxyl group or a leaving group, and k5 and k6 are numbers satisfying the following conditions: $1 \leq k5 \leq (k+2)/2$, and $k5+k6=k+2$. In the polyglycerin compound represented by the formula (4), Y represents hydroxyl group or a leaving group. In the specification, the "leaving group" is a group which imparts to the polyglycerin compound reactivity with a phospholipid, and includes electron withdrawing groups and other groups. Specifically, examples of such a group include imidazole group, 4-nitrophenyloxy group, benzotriazole group, chlorine, methoxy group, ethoxy group, propyloxy group, carbonyloxcy-N-2-pyrrolidinone group, carbonyl- 2-oxypyrimidine group, N-succinimidyloxy group, pentafluorobenzoyl group, and the like. Among them, imidazole group, 4-nitrophenyloxy group, benzotriazole group, chlorine, and N-succinimidyloxy group are preferred, and N-succinimidyloxy group and 4-nitrophenyloxy group are particularly preferred.

Examples of the method for obtaining the polyglycerin compound represented by the formula (4) include, for example, a method of introducing the aforementioned leaving group into the polyglycerin compound by using an activating agent such as N,N'-succinimidyl carbonate and chloroformic acid p-nitrophenyl ester in an organic solvent in the presence of a basic catalyst such as triethylamine or dimethylaminopyridine, and the like. However, the method is not limited to the above method, and the polyglycerin compound represented by the formula (4) may be produced by any kind of method. An amount of the activating agent may generally be equimolar or more of k1 as being the number of the phospholipid to be introduced. However, the amount may preferably be 1 to 2 moles based on the number of k1 substantially considering a purity of the activating agent and the like.

The phospholipid, which is used to synthesize the compound of the present invention represented by the formula (1) wherein a and b are 0 by using the polyglycerin compound represented by the formula (4), is represented by the formula (5). This phospholipid may be a natural phospholipid or synthetic phospholipid. Examples include, for example, natural and synthetic phosphatidylethanolamines such as soybean phosphatidyldiethanolamine and hydrogenated soybean phosphatidyldiethanolamine, yolk phosphatidyldiethanolamine and hydrogenated yolk phosphatidyldiethanolamine, and the like. A basic catalyst can be used for this reaction, and the type of the basic catalyst is not particularly limited. Examples include, for example, nitrogen-containing substances such as triethylamine, dimethylaminopyridine, and ammonium acetate, organic salts such as sodium phosphate, sodium carbonate, sodium hydrogencarbonate, sodium borate, and sodium acetate, and the like. An amount of the basic catalyst is not particularly limited, and may be, for example, 1 to 5 moles, preferably 1 to 2 moles, per mole of the phospholipid compound used in the step (B). An amount of the phospholipid compound used in the step (B) is not particularly limited, and can be suitably reacted depending on the objective number of k1. For example, the amount may preferably be 1 to 3 moles, more preferably 1 to 1.3 moles based on the number of k1 for one molecule.

As the organic solvent used for this reaction, those having no functional group such as hydroxyl group can be used without particular limitation. Examples include, for example, ethyl acetate, dichloromethane, chloroform, benzene, dimethyl sulfoxide (DMSO), toluene, and the like. Among them, chloroform, DMSO, and toluene are preferred. Organic solvents having hydroxyl group such as ethanol will react with the leaving group at the end of the polyglycerin compound represented by the formula (4), and therefore they are not preferred. Although dichloromethane and the like do not have a problem concerning reactivity, they may not be practically preferred due to a low boiling point. A reaction temperature of this reaction is not particularly limited, and may be, for example, 20 to 110° C., preferably 30 to 90° C. A reaction time is not particularly limited and may desirably be, for example, 1 hour or more, preferably 2 to 24 hours. A reaction temperature below 20° C. may not be preferred from a viewpoint of reaction efficiency, and at a reaction temperature higher than 90° C., the acyl group of the phospholipid compound used for the reaction may be hydrolyzed.

By using the compound of the present invention represented by the aforementioned formula (1) as a surfactant, a solubilized solution, emulsion, and dispersion can be obtained. The compound of the present invention is particularly useful as a solubilizer, emulsifier, or dispersing agent for hardly water-soluble medicaments. When the surfactant of the present invention is used as an emulsifier, solubilizer, or dispersing agent, the emulsifier, solubilizer, or dispersing agent may solely contain the surfactant of the present invention, or may also contain other known components used for emulsification, solubilization, or dispersion. The form of the solubilized solution or dispersion is not limited, and examples include a solution in which a fat-soluble substance or the like is dissolved in a dispersion medium such as water and a buffer, or a dispersion in which a fat-soluble substance or the like is dispersed in a dispersion medium such as water and a buffer and the like.

Formulation of the emulsion and solubilized solution are not limited, and examples include a micelle solution formed with the surfactant of the present invention, i.e., a micelle solution in which micelles contain a fat-soluble substance in the inside thereof, an emulsion in which dispersed particles formed with the surfactant of the present invention and a fat-soluble substance or the like exist as colloidal particles or larger particles, and the like. Examples of the micelle solution include polymer micelle solutions in which dispersed particles have a diameter of 10 to 300 nm. The emulsion may be of O/W type or W/O/W type. The fat-soluble substance that can be solubilized or emulsified is not particularly limited, and examples thereof include a higher alcohol, ester oil, triglycerin, tocopherol, higher fatty acid, hardly water-soluble medicaments, and the like.

The hardly water-soluble medicaments to be solubilized according to the present invention are not particularly limited, and those having a solubility of 1,000 ppm or less in water at 25° C., those having a solubility of 10 mg/mL or less and the like are used, for example. Examples of the hardly water-soluble medicaments include, for example, cyclosporin, amphotericin B, indomethacin, nifedipine, tacrolimus, melphalan, ifosfamide, streptozocin (streptozotocin), methotrexate, fluorouracil, cytarabine, tegafur, idoxido, paclitaxel, docetaxel, daunorubicin, bleomycin, medroxyprogesterone, phenofibrate, and the like.

The use as a dispersing agent in the field of cosmetics is also not particularly limited. For example, when a water-soluble substance such as ascorbic acid is retained in an internal aqueous phase of a lipid membrane structure, a fat-soluble substance such as tocopherol is retained in a lipid bilayer or the like, the objective substance can be more stably dispersed in an aqueous solution by using the compound of the present invention as a lipid membrane structure formulating agent. When the compound is used as a surfactant or a dispersing agent, the amount of the compound of the present invention to be added is 0.1 to 20% by mass, preferably 0.5 to 7% by mass, more preferably 0.5 to 5% by mass, based on a total mass of an objective substance for solubilization, dispersion, emulsification or the like.

Further, for solubilization of the hardly water-soluble medicament, an amount of the compound of the present invention varies depending on the solubility of the medicament and the like, and the amount may be decided depending on the solubility. Although the amount of the compound of the present invention is not limited to the following amount, the amount may be, for example, 500 to 100,000% by mass relative to the total mass of an objective medicament.

The compounds of the aforementioned formula (1) wherein k2 is 0 can be especially effectively used as a non-ionic surfactant under a high salt concentration condition. Generally, polyglycerin-modified phospholipids and the like have hydrophilicity deriving from the glycerin group and hydrophobicity deriving from the acyl group, and therefore they can be used as surfactants. However, surfactants having oxyalkylene groups represented by polyalkylene oxide-modified phospholipids generally have a problem in that they produce turbidity when they are used under a high salt concentration condition. In addition, the use of nonionic type surfactants consisting of glycidol derivatives under a high salt concentration condition has been reported. However, such surfactants have a problem of skin irritation and the like, and thus have a problem of unsuitability for application in the cosmetic field. The compounds represented by the aforementioned formula (1) have a characteristic feature in that they can maintain high solubilization ability even under a condition of high salt concentration, and can be used as a surfactant having superior salt tolerance. Moreover, they can be used as a surfactant highly compatible with the skin in the field of cosmetics.

The compounds of the aforementioned formula (1) wherein k2 is more than 0, i.e., compounds having carboxyl group at the end of branched glycerin group, can be used as a pH sensitive phospholipid, for example, as a dispersing agent. When a cationic substance (e.g., physiologically active cationic substance) or a basic substance, is dispersed in water, it can be stably dispersed in water by, for example, coating the surfaces of microparticles or the like containing the cationic substance or basic substance with the aforementioned compound. The compound of the present invention has polyanionic groups, and thereby enables stable dispersion by ionic bonds.

The compounds of the present invention represented by the aforementioned formula (1) can be used as phospholipids constituting a lipid membrane structure such as liposome, emulsion, and micelle. By using the compounds of the present invention, curculating time in blood of a lipid membrane structure, preferably liposome, can be increased. This effect can be attained by adding a small amount of the compound of the present invention to a lipid membrane structure. Although it is not intended to be bound by any specific theory, it is considered that, when the compounds of the present invention having 4 or more of multiple branches are used as a phospholipid constituting lipid membrane structure, the polyglycerin chains three-dimensionally spread in the membranes of lipid membrane structure, and therefore aggregation of microparticles in an aqueous solution is prevented to achieve a stable dispersion state.

The amount of the compound of the present invention added to a lipid membrane structure may be an amount sufficient for effectively expressing efficacy of a medicament in vivo and is not particularly limited. The amount can be suitably selected depending on, for example, a type of medicament to be retained by the lipid membrane structure, a purpose of therapeutic or prophylactic treatment and the like, and a form of the lipid membrane structure. A type of a medicament retained by the lipid membrane structure provided by the present invention is not particularly limited. For example, compounds used as antitumor agents are preferred. Examples of such compounds include, for example, camptothecin derivatives such as irinotecan hydrochloride, nogitecan hydrochloride, exatecan, RFS-2000, lurtotecan, BNP-1350, Bay-383441, PNU-166148, IDEC-132, BN-80915, DB-38, DB-81, DB-90, DB-91, CKD-620, T-0128, ST-1480, ST-1481, DRF-1042 and DE-310, taxane derivatives such as docetaxel hydrate, paclitaxel, IND-5109, BMS-184476, BMS-188797, T-3782, TAX-1011, SB-RA-31012, SBT-1514 and DJ-927, ifosfamide, nimustine hydrochloride, carboquone, cyclophosphamide, dacarbazine, thiotepa, busulfan, melphalan, ranimustine, estramustine phosphate sodium, 6-mercaptopurine riboside, enocitabine, gemcitabine hydrochloride, carmofur, cytarabine, cytarabine ocphosphate, tegafur, doxifluridine, hydroxycarbamide, fluorouracil, methotrexate, mercaptopurine, fludarabine phosphate, actinomycin D, aclarubicin hydrochloride, idarubicin hydrochloride, epirubicin hydrochloride, daunorubicin hydrochloride, doxorubicin hydrochloride, pirarubicin hydrochloride, bleomycin hydrochloride, zinostatin stimalamer, neocarzinostatin, mytomycin C, bleomycin sulfate, peplomycin sulfate, etoposide, vinorelbine tartrate, vincristine sulfate, vindesine sulfate, vinblastine sulfate, amrubicin hydrochloride, gefitinib, exemestan, capecitabine, TNP-470, TAK-165, KW-2401, KW-2170, KW-2871, KT-5555, KT-8391, TZT-1027, S-3304, CS-682, YM-511, YM-598, TAT-59, TAS-101, TAS-102, TA-106, FK-228, FK-317, E7070, E7389, KRN-700, KRN-5500, J-107088, HMN-214, SM-11355, ZD-0473 and the like.

Further, a gene or the like may be encapsulated in the lipid membrane structure of the present invention. The gene may be any of oligonucleotide, DNA, and RNA, and in particular, examples thereof include a gene for in vitro gene introduction such as transformation and a gene that act upon in vivo expression, for example, a gene for gene therapy, gene used in breeding of industrial animals such as laboratory animals and livestock, and the like. Examples of the gene for gene therapy include an antisense oligonucleotide, antisense DNA, antisense RNA, gene coding for a physiologically active substance such as enzymes and cytokines, and the like.

The aforementioned lipid membrane structure may further contain phospholipids and a sterol such as cholesterol, and cholestanol, another fatty acid having a saturated or unsaturated acyl group having 8 to 24 carbon atoms and an antioxidant such as α-tocopherol. Examples of the phospholipid include phosphatidylethanolamine, phosphatidylcholine, phosphatidylserine, phosphatidylinositol, phosphatidylglycerin, cardiolipin, sphingomyelin, ceramide phosphorylethanolamine, ceramide phosphorylglycerin, ceramide phosphorylglycerin phosphate, 1,2-dimyristoyl-1,2-deoxyphosphatidylcholine, plasmalogen, phosphatidic acid and the like, and they may be used alone or two or more kind of them can be used in combination. The fatty acid residues of these phospholipids are not particularly limited, and examples thereof include a saturated or unsaturated fatty acid residue having 12 to 20 carbon atoms. Specific examples include an acyl group derived from a fatty acid such as lauric acid, myristic acid, palmitic acid, stearic acid, oleic acid and linoleic acid. Further, phospholipids derived from natural products such as egg yolk lecithin and soybean lecithin can also be used.

The form of the lipid membrane structure of the present invention and the preparation method thereof are not particularly limited, and examples of the existence form thereof include, for example, a form of dried lipid mixture, form of dispersion in an aqueous solvent, dried or frozen form of the foregoing form and the like. The lipid membrane structure in the form of dried lipid mixture can be prepared by, for example, first dissolving lipid components to be used in an organic solvent such as chloroform, and drying up the solution under reduced pressure by using an evaporator or spray-drying the solution by using a spray dryer. Examples of the form of the lipid membrane structure dispersed in an aqueous solvent include unilamella liposomes, multilamella liposomes, O/W type emulsion, W/O/W type emulsion, spherical micelles, worm-like micelles, irregular layered structure and the like, and liposomes are preferred among them. A size of the lipid membrane structure in the dispersed state is not particularly limited. For example, the particle diameter of liposome or particle in emulsion is 50 nm to 5 μm, and the particle diameter of spherical micelle is 5 to 100 nm. When a worm-like micelle or irregular layered structure is formed, it can be considered that the thickness of one layer thereof is 5 to 10 nm, and such layers form a single layer.

The composition of the aqueous solvent (dispersion medium) is also not particularly limited, and the aqueous solvent may be, for example, a buffer such as phosphate buffer, citrate buffer, and phosphate-buffered physiological saline, physiological saline, a medium for cell culture or the like. The lipid membrane structure can be stably dispersed in these aqueous solvents. An aqueous solution of a sugar such as glucose, lactose, and sucrose, an aqueous solution of a polyhydric alcohol such as glycerin and propylene glycol and the like may be further added. In order to stably store the lipid membrane structure dispersed in such an aqueous solvent for a long period of time, it is desirable to minimize electrolytes in the aqueous solvent from a viewpoint of physical stability such as prevention of aggregation. Further, from a viewpoint of chemical stability of lipids, it is desirable to control a pH of the aqueous solvent to be in a range of from weakly acidic pH to around neutral pH (pH 3.0 to 8.0), and to remove dissolved oxygen by nitrogen bubbling. Further, when a lyophilized or spray-dried product is stored, for example, use of an aqueous sugar solution or aqueous polyhydric alcohol solution may enable effective storage at lyophilization and storage of an aqueous sugar solution. A concentration of these aqueous solvents is not particularly limited. When an aqueous sugar solution is used, for example, the concentration is preferably 2 to 20% (W/V), more preferably 5 to 10% (W/V), and when an aqueous polyhydric alcohol solution is used, the concentration is preferably 1 to 5% (W/V), more preferably 2 to 2.5% (W/V). In a buffer, a concentration of the buffering agent is preferably 5 to 50 mM, more preferably 10 to 20 mM. A concentration of the lipid membrane structure in an aqueous solvent is not particularly limited. A concentration of the total amount of lipids in the lipid membrane structure is preferably 0.1 to 500 mM, more preferably 1 to 100 mM.

The formulation of the lipid membrane structure dispersed in an aqueous solvent can be prepared by adding the aforementioned dried lipid mixture to an aqueous solvent and emulsifying the mixture by using an emulsifier such as a homogenizer, ultrasonic emulsifier, high pressure jet emulsifier or the like. Further, the aforementioned form can also be prepared by a method known as a method for preparing liposomes, for example, the reverse phase evaporation method, and the method for preparing dispersion is not particularly limited. When it is desired to control a size of the lipid membrane structure, extrusion (extrusion filtration) can be performed under high pressure by using a membrane filter of even pore sizes or the like.

Examples of the method for drying the aforementioned lipid membrane structure dispersed in an aqueous solvent include ordinary lyophilization and spray drying. As the aqueous solvent used for these operations, an aqueous sugar solution, preferably aqueous sucrose solution or aqueous lactose solution, may be used as described above. When a lipid membrane structure dispersed in the aqueous solvent is first prepared and then successively dried, it becomes possible to store the lipid membrane structure for a long period of time. In addition, when an aqueous solution of a medicament is added to the dried lipid membrane structure, the lipid mixture is efficiently hydrated and thereby the medicament can be efficiently retained in the lipid membrane structure, which provides an advantageous effect. For example, a pharmaceutical composition can be prepared by adding a medicament to the lipid membrane structure, and thus the lipid membrane structure can be used as a pharmaceutical composition for therapeutic treatment and/or prevention of a disease. When the medicament is a gene, the composition can also be used as a gene delivery kit.

As for a formulation of the pharmaceutical composition, the formulation may be the lipid membrane structures retaining a medicament, as well as a mixture of a medicament and the lipid membrane structures. The term "retain" used herein means that a medicament exists inside the membranes of the lipid membrane structures, on the membrane surfaces, in the membranes, in the lipid layers, and/or on the lipid layer surfaces. An available formulation of the pharmaceutical composition and a method for preparation thereof are not particularly limited in the same manner as the lipid membrane structures. As for the available form, examples include a form of a dried mixture, a form of a dispersion in an aqueous solvent, and forms obtained by further drying or freezing said forms.

A dried mixture of lipids and a medicament can be produced by, for example, once dissolving lipid components and a medicament to be used in an organic solvent such as chloroform and then subjecting the resulting solution to solidification under reduced pressure by using an evaporator or spray drying by using a spray dryer. Examples of a form in which a mixture of lipid membrane structures and a medicament are dispersed in an aqueous solvent include, but not particularly limited thereto, multi-lamella liposomes, unilamella liposomes, O/W type emulsions, W/O/W type emulsions, spherical micelles, fibrous micelles, layered structures of irregular shapes and the like. A size of particles (particle diameter) as the mixture, a composition of the aqueous solvent and the like are not particularly limited. For example, liposomes may have a size of 50 nm to 2 μm, spherical micelles may have a size of 5 to 100 nm, and emulsions may have a particle diameter of 50 nm to 5 μm. A concentration of the mixture in the aqueous solvent is also not particularly limited. Several methods are known as methods for producing a mixture of lipid membrane structures and a medicament in the form of dispersion in an aqueous solvent. It is necessary to appropriately chose a suitable method depending on an available form of the mixture of lipid membrane structures and a medicament.

<Production Method 1>

Production Method 1 is a method of adding an aqueous solvent to the aforementioned dried mixture of lipids and a medicament and emulsifying the mixture by using an emulsifier such as homogenizer, ultrasonic emulsifier, high-pressure injection emulsifier, or the like. When it is desired to control the size (particle diameter), extrusion (extrusion filtration) can be further performed under a high pressure by using a membrane filter having uniform pore sizes. In this method, in order to prepare a dried mixture of lipids and a medicament first, it is necessary to dissolve the medicament in an organic solvent, and the method has an advantage that it can make the best utilization of interactions between the medicament and lipid membrane structures. Even when the lipid membrane structures have a layered structure, a medicament can enter into the inside of the multiple layers, and thus use of this method generally provides a higher retention ratio of the medicament in the lipid membrane structures.

<Production Method 2>

Production Method 2 is a method of adding an aqueous solvent containing a medicament to dried lipid components obtained by dissolving the lipid components in an organic solvent and evaporating the organic solvent, and emulsifying the mixture. When it is desired to control the size (particle diameter), extrusion (extrusion filtration) can be further performed under a high pressure by using a membrane filter having uniform pore sizes. This method can be used for a medicament that is hardly dissolved in an organic solvent, but can be dissolved in an aqueous solvent. When the lipid membrane structures are liposomes, they have an advantage that they can retain a medicament also in the part of internal aqueous phase.

<Production Method 3>

Production Method 3 is a method of further adding an aqueous solvent containing a medicament to lipid membrane structures such as liposomes, emulsions, micelles or layered structures already dispersed in an aqueous solvent. This method is limitedly applied to a water-soluble medicament. The addition of a medicament to already prepared lipid membrane structures is performed from the outside. Therefore, when the medicament is a polymer, the medicament cannot enter into the inside of the lipid membrane structures, and the medicament may be present in a form that it binds to the surfaces of lipid membrane structures. When liposomes are used as the lipid membrane structures, use of Production Method 3 may result in formation of a sandwich-like structure in which the medicament is sandwiched between liposome particles (generally called as a complex). An aqueous dispersion of lipid membrane structures alone is prepared beforehand in this production method. Therefore, decomposition of a medicament during the preparation need not be taken into consideration, and a control of the size (particle diameter) is also readily operated, which enables relatively easier preparation compared with Production Methods 1 and 2.

<Production Method 4>

Production Method 4 is a method of further adding an aqueous solvent containing a medicament to a dried product obtained by once producing lipid membrane structures dispersed in an aqueous solvent and then drying the same. In this method, a medicament is limited to a water-soluble medicament in the same manner as Production Method 3. A significant difference from Production Method 3 is a mode of presence of the lipid membrane structures and a medicament. That is, in Production Method 4, lipid membrane structures dispersed in an aqueous solvent are once produced and further dried to obtain a dried product, and at this stage, the lipid membrane structures are present in a state of a solid as fragments of lipid membranes. In order to allow the fragments of lipid membranes to be present in a solid state, it is preferable to use an aqueous solution of a sugar, preferably an aqueous solution of sucrose or aqueous solution of lactose, as the aqueous solvent as described above. In this method, when the aqueous solvent containing a medicament is added, hydration of the fragments of the lipid membranes present in a state of a solid quickly starts with the invasion of water, and thus the lipid membrane structures can be reconstructed. At this time, a structure of a form in which a medicament is retained in the inside of the lipid membrane structures can be produced.

In Production Method 3, when a medicament is a polymer, the medicament cannot enter into the inside of the lipid membrane structures, and is present in a mode that it binds to the surfaces of the lipid membrane structures. Production Method 4 significantly differs in this point. In Production Method 4, an aqueous dispersion of lipid membrane structures alone is prepared beforehand, and therefore, decomposition of the medicament during the emulsification need not be taken into consideration, and a control of the size (particle diameter) is also easy attainable. For this reason, said method enables relatively easier preparation compared with Production Methods 1 and 2. Besides the above mentioned advantages, this method also has advantages that storage stability for a pharmaceutical preparation is easily secure, because the method uses lyophilization or spray drying; when the dried preparation is rehydrated with an aqueous solution of a medicament, original size (particle diameter) can be reproduced; when a polymer medicament is used, the medicament can be easily retained in the inside of the lipid membrane structures and the like.

As other method for producing a mixture of lipid membrane structures and a medicament in a form of a dispersion in an aqueous solvent, a method well known as that for producing liposomes, e.g., the reverse phase evaporation method or the like, may be separately used. When it is desired to control the size (particle diameter), extrusion (extrusion filtration) can be performed under a high pressure by using a membrane filter having uniform pore sizes. Further, examples of the method for further drying a dispersion, in which the aforementioned mixture of lipid membrane structures and a medicament is dispersed in an aqueous solvent, include lyophilization and spray drying. As the aqueous solvent in this process, it is preferable to use an aqueous solution of a sugar, preferably an aqueous solution of sucrose or an aqueous solution of lactose. Examples of the method for further freezing a dispersion, in which the aforementioned mixture of lipid membrane structures and a medicament is dispersed in an aqueous solvent, include ordinary freezing methods. As the aqueous solvent in this process, it is preferable to use an aqueous solution of sugar or aqueous solution of polyhydric alcohol in the same manner as the solution for the lipid membrane structures alone.

Lipids that can be added to the pharmaceutical composition may be suitably chosen depending on a type of a medicament to be used and the like. The lipids are used in an amount of, for example, 0.1 to 1000 parts by mass, preferably 0.5 to 200 parts by mass, based on 1 part by mass of a medicament when the medicament is not a gene. When the medicament is a gene, the amount is preferably 1 to 500 nmol, more preferably 10 to 200 nmol, with 1 μg of a medicament (gene).

The method for use of the pharmaceutical composition of the present invention which contains the lipid membrane structures may be suitably considered depending on a form thereof. The administration route for humans is not particularly limited, and either oral administration or parenteral administration may be used. Examples of dosage forms for oral administration include, for example, tablets, powders, granules, syrups, capsules, solutions for internal use and the like, and examples of dosage forms for parenteral administration include, for example, injections, drip infusion, eye drops, ointments, suppositories, suspensions, cataplasms, lotions, aerosols, plasters and the like. In the medicinal field, injections or drip infusion is preferred among them, and as the administration method, intravenous injection, subcutaneous injection and intradermal injection, as well as local injection to targeted cells or organs are preferred. Further, as for the cosmetic field, examples of forms of cosmetics include lotions, creams, toilet water, milky lotions, foams, foundations, lipsticks, packs, skin cleaning agents, shampoos, rinses, conditioners, hair tonics, hair liquids, hair creams and the like.

EXAMPLES

The present invention will be explained more specifically with reference to the following examples. However, the scope of the present invention is not limited to these examples. In the chemical formulas shown in the following examples, the indications of PG(6), PG(8) and the like mean hexaglycerin, octaglycerin and the like, respectively, which are polyglycerin mixtures having average polymerization degrees of 6, 8 and the like, respectively.

Synthesis Example 1

(1) Preparation of Distearoylphosphatidylethanolamine Succinate

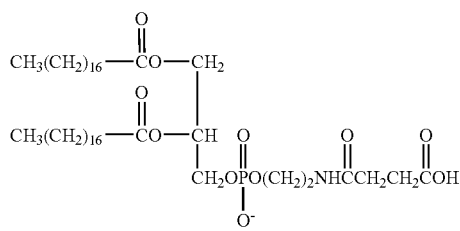

Distearoylphosphatidylethanolamine (20.0 g, 26.7 mmol) was added with 150 mL of chloroform, stirred at 55° C., and added with 2.2 g (267 mmol) of sodium acetate to obtain a phospholipid solution in chloroform. The solution was added with 3.5 g (34.8 mmol) of succinic anhydride and reacted at 55° C. for 3 hours. Completion of the reaction was confirmed by thin layer chromatography (TLC) utilizing a silica gel plate where no distearoylphosphatidylethanolamine was detected by ninhydrin coloration. As the developing solvent, a mixed solvent of chloroform and methanol at a volume ratio of 85:15 was used. After the reaction, the solution was filtered to remove sodium acetate, and then the filtrate was concentrated. After the concentration of the filtrate, the residue was added with isopropyl alcohol (100 mL), and stirred at room temperature for 30 minutes. The crystals were collected by filtration, then washed with hexane (80 mL), collected by filtration, and dried to obtain crystals of distearoylphosphatidylethanolamine succinate (20.5 g).

Synthesis Example 2

(2) Preparation of Distearoylphosphatidylethanolamine Glutarate

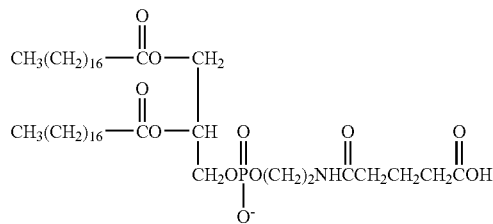

Distearoylphosphatidylethanolamine (20.0 g, 26.7 mmol) was added with 150 mL of chloroform, stirred at 55° C., and added with 2.2 g (267 mmol) of sodium acetate to obtain a phospholipid solution in chloroform. The solution was added with 4.0 g (34.8 mmol) of glutaric anhydride and reacted at 55° C. for 3 hours. Completion of the reaction was confirmed by TLC in the same manner as described above. After the reaction, the solution was filtered to remove sodium acetate, and then the filtrate was concentrated. After the concentration of the filtrate, the residue was added with isopropyl alcohol (100 mL), and stirred at room temperature for 30 minutes. The crystals were collected by filtration, washed with hexane (80 mL), collected by filtration, and dried to obtain crystals of distearoylphosphatidylethanolamine glutarate (19.8 g).

Example 1

(3) Preparation of Hexaglycerol Glutaryl Distearoylphosphatidylethanolamine (6)

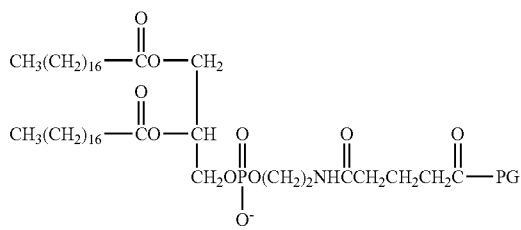

Distearoylphosphatidylethanolamine glutarate (4.3 g, 5.0 mmol) was added with chloroform (25 mL) and stirred at 45° C. The chloroform solution was added with 11.6 g (25 mmol) of hexaglycerin dissolved in dimethyl sulfoxide (10 mL), and then added with 2.1 g (10 mmol) of dicyclohexylcarbodiimide and 0.6 g (5.3 mmol) of dimethylaminopyridine. The reaction was performed at 45° C. for 2 hours. Completion of the reaction was confirmed by TLC, namely, confirmed by thin layer chromatography (TLC) utilizing a silica gel plate where no distearoylphosphatidylethanolamine glutarate was detected. As the developing solvent, a mixed solvent of chloroform, methanol and water at a volume ratio of 65:25:4 was used. After the completion of the reaction, the deposited dicyclohexylurea was removed by filtration, and then the filtrate was passed through a cation exchange resin (DIAION SK1BH) filled in a column. The eluate was collected in aqueous disodium hydrogenphosphate added with a small amount of methanol for neutralization. The eluate was dehydrated over sodium sulfate, then filtered, and concentrated. The residue was crystallized 3 times from chloroform/acetone/dimethyl sulfoxide, or acetone/dimethyl sulfoxide to obtain 4.8 g of crystals of hexaglycerol glutaryl distearoylphosphatidylethanolamine.

By $^1$H-NMR (CDCl$_3$), protons of methyl group at the end of the stearoyl group at δ 0.88, protons of methylene group of the stearoyl group at δ 1.26, protons of methylene group of —NH(C=O)CH$_2$CH$_2$CH$_2$COO— derived from glutaric acid at δ 1.95, protons of methylene group of —NH(C=O)CH$_2$CH$_2$CH$_2$COO— at δ 2.29 and 2.31, methylene protons and methine protons derived from hexaglycerin at δ 3.2-4.5 were observed.

Example 2

(4) Preparation of Octaglycerol Glutaryl Distearoylphosphatidylethanolamine (8)

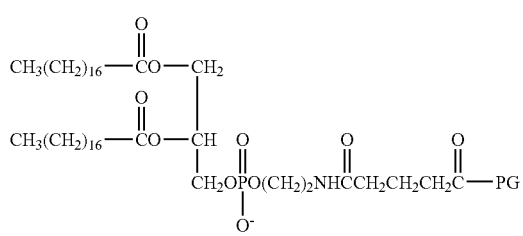

Distearoylphosphatidylethanolamine glutarate (4.3 g, 5.0 mmol) was added with chloroform (25 mL) and stirred at 45° C. This chloroform solution was added with 15.3 g (25 mmol) of octaglycerin dissolved in dimethyl sulfoxide (20 mL), and then added with 2.1 g (10 mmol) of dicyclohexylcarbodiimide and 0.6 g (5.3 mmol) of dimethylaminopyridine. The reaction was performed at 45° C. for 2 hours. Completion of the reaction was confirmed by TLC in the same manner as described above. After the completion of the reaction, the deposited dicyclohexylurea was removed by filtration, and then the filtrate was passed through a cation exchange resin (DIAION SK1BH) filled in a column. The eluate was collected in aqueous disodium hydrogenphosphate added with a small amount of methanol for neutralization. The eluate was dehydrated over sodium sulfate, then filtered and concentrated. The residue was crystallized 3 times from chloroform/acetone/dimethyl sulfoxide, or acetone/dimethyl sulfoxide to obtain 4.5 g of crystals of octaglycerol glutaryl distearoylphosphatidylethanolamine.

By $^1$H-NMR (CDCl$_3$), protons of methyl group at the end of the stearoyl group at δ 0.88, protons of methylene group of the stearoyl group at δ 1.26, protons of methylene group of —NH(C=O)CH$_2$CH$_2$CH$_2$COO— derived from glutaric acid at δ 1.95, protons of methylene group of —NH(C=O)CH$_2$CH$_2$CH$_2$COO— at δ 2.29 and 2.31, methylene protons and methine protons derived from octaglycerin at δ 3.2-4.5 were observed.

Example 3

(5) Preparation of Decaglycerol Glutaryl Distearoylphosphatidylethanolamine

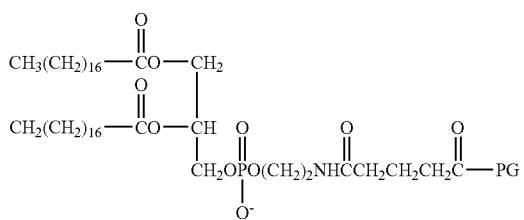

(10)

Distearoylphosphatidylethanolamine glutarate (4.3 g, 5.0 mmol) was added with chloroform (25 mL) and stirred at 45° C. The chloroform solution was added with 19.0 g (25 mmol) of decaglycerin dissolved in dimethyl sulfoxide (20 mL), and then added with 2.1 g (10 mmol) of dicyclohexylcarbodiimide and 0.6 g (5.3 mmol) of dimethylaminopyridine. The reaction was performed at 45° C. for 2 hours. Completion of the reaction was confirmed by TLC in the same manner as described above. After the completion of the reaction, the deposited dicyclohexylurea was removed by filtration, and then the filtrate was passed through a cation exchange resin (DIAION SK1BH) filled in a column. The eluate was collected in aqueous disodium hydrogenphosphate added with a small amount of methanol for neutralization. The eluate was dehydrated over sodium sulfate, then filtered and concentrated. The residue was crystallized 3 times from chloroform/acetone/dimethyl sulfoxide, or acetone/dimethyl sulfoxide to obtain 4.3 g of crystals of decaglycerol glutaryl distearoylphosphatidylethanolamine.

By $^1$H-NMR (CDCl$_3$), protons of methyl group at the end of the stearoyl group at δ 0.88, protons of methylene group of the stearoyl group at δ 1.26, protons of methylene group of —NH(C=O)CH$_2$CH$_2$CH$_2$COO— derived from glutaric acid at δ 1.95, protons of methylene group of —NH(C=O)CH$_2$CH$_2$CH$_2$COO— at δ 2.29 and 2.31, methylene protons and methine protons derived from decaglycerin at δ 3.2-4.5 were observed.

Example 4

(6) Preparation of Octaglycerol Succinyl Distearoylphosphatidylethanolamine

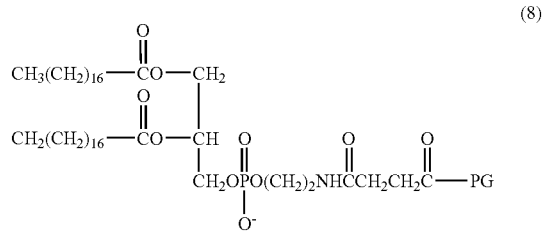

(8)

Distearoylphosphatidylethanolamine succinate (4.2 g, 5.0 mmol) was added with chloroform (10 mL) and stirred at 45° C. The chloroform solution was added with 15.3 g (25 mmol) of octaglycerin dissolved in dimethyl sulfoxide (20 mL), and then added with 2.1 g (10 mmol) of dicyclohexylcarbodiimide and 0.6 g (5.3 mmol) of dimethylaminopyridine. The reaction was performed at 45° C. for 2 hours. Completion of the reaction was confirmed by thin layer chromatography (TLC) utilizing a silica gel plate where no distearoylphosphatidylethanolamine succinate was detected. As the developing solvent, a mixed solvent of chloroform, methanol and water at a volume ratio of 65:25:4 was used. After the completion of the reaction, the deposited dicyclohexylurea was removed by filtration, and then the filtrate was passed through a cation exchange resin (DIAION SK1BH) filled in a column. The eluate was collected in aqueous disodium hydrogenphosphate added with a small amount of methanol for neutralization. The eluate was dehydrated over sodium sulfate, then filtered and concentrated. The residue was crystallized 3 times from chloroform/acetone/dimethyl sulfoxide, or acetone/dimethyl sulfoxide to obtain 4.8 g of crystals of octaglycerol succinyl distearoylphosphatidylethanolamine.

By $^1$H-NMR (CDCl$_3$), protons of methyl group at the end of the stearoyl group at δ 0.88, protons of methylene group of the stearoyl group at δ 1.26, protons of methylene group of —NH(C=O)CH$_2$CH$_2$COO— derived from succinic acid at δ 2.29 and 2.31, methylene protons and methine protons derived from octaglycerin at δ 3.2-4.5 were observed.

Example 5

(7) Preparation of Tetradecaglycerol Succinyl Distearoylphosphatidylethanolamine

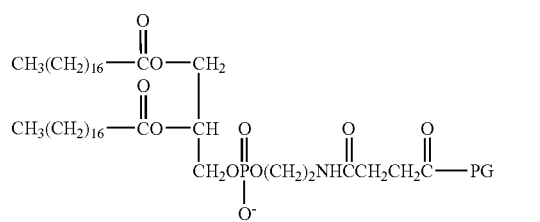

(40)

Distearoylphosphatidylethanolamine succinate (1.7 g, 2.0 mmol) was added with chloroform (10 mL) and stirred at 45° C. This chloroform solution was added with 29.8 g (10 mmol) of tetradecaglycerin dissolved in dimethyl sulfoxide (40 mL), and then added with 0.8 g (4.0 mmol) of dicyclohexylcarbodiimide and 0.3 g (2.1 mmol) of dimethylaminopyridine. The reaction was performed at 45° C. for 2 hours. Completion of the reaction was confirmed by TLC in the same manner as described above. After the completion of the reaction, the deposited dicyclohexylurea was removed by filtration, and then the filtrate was passed through a cation exchange resin (DIAION SK1BH) filled in a column. The eluate was collected in aqueous disodium hydrogenphosphate added with a small amount of methanol for neutralization. The eluate was dehydrated over sodium sulfate, then filtered and concentrated. The residue was crystallized 3 times from chloroform/acetone/dimethyl sulfoxide, or acetone/dimethyl sulfoxide to obtain 3.8 g of crystals of tetradecaglycerol succinyl distearoylphosphatidylethanolamine.

By $^1$H-NMR (CDCl$_3$), protons of methyl group at the end of the stearoyl group at δ 0.88, protons of methylene group of the stearoyl group at δ 1.26, protons of methylene group of —NH(C═O)CH$_2$CH$_2$COO— derived from succinic acid at δ 2.29 and 2.31, methylene protons and methine protons derived from tetradecaglycerin at δ 3.2-4.5 were observed.

Example 6

Evaluation as Long Circulating Liposome in Blood (1) Preparation of Liposomes

Each of the lipids mentioned in each of the membrane compositions shown in Table 1 (Examples 1 to 5, Control Examples 1 to 4) were weighed in each ratio and dissolved in a chloroform/methanol mixture (2:1), then the organic solvents were evaporated by using an evaporator, and further the residue was dried under reduced pressure for 1 hour. Then, the dried lipids (lipid film) were added with 10 mL of 155 mM aqueous ammonium sulfate (pH 5.5) heated at 65° C. beforehand, and the mixture was lightly stirred by using a vortex mixer on a hot water bath (until lipid was substantially peeled off from a recovery flask). This lipid dispersion was transferred to a homogenizer, homogenized for 10 strokes and sized by using polycarbonate membrane filters with various pore sizes (0.2 μm×3 times, 0.1 μm×3 times, 0.05 μm×3 times and 0.03 μm×3 times) to prepare a dispersion of empty liposomes having a particle diameter of about 100 nm.

In an amount of 4 mL of this empty liposome dispersion was diluted 2.5 times with physiological saline, and the resulting diluted liposome dispersion was placed in an ultracentrifugation tube and centrifuged at 65,000 rpm for 1 hour. Then, the supernatant was discarded, and the precipitates were resuspended in physiological saline to make the dispersion volume 10 mL, the volume of the liposome dispersion before the centrifugation (at this time point, the total lipid concentration was adjusted to 50 mM). The aforementioned empty liposome dispersion in which the external aqueous phase was replaced with physiological saline (total lipid concentration: 50 mM) and a doxorubicin solution (medicament concentration: 3.3 mg/mL physiological saline) were heated beforehand at 60° C., and the empty liposome dispersion and the doxorubicin solution were added at a volume ratio of 4:6 (i.e., final medicament concentration: 2.0 mg/mL, final lipid concentration, 20 mM) and incubated at 60° C. for 1 hour. The mixture was further cooled at room temperature to obtain a doxorubicin-containing liposome dispersion.

(2) Physical Properties of the Liposome

The percentage of doxorubicin retained by the liposomes was obtained by collecting a part of the aforementioned liposome dispersion, subjecting the sample to gel filtration (Sephadex G-50, mobile phase was physiological saline), and then quantifying doxorubicin in the liposome fraction eluted in the void volume by using liquid chromatography. Further, particle diameter was determined by measurement based on the quasi-elastic light scattering (QELS) method performed for a part of the aforementioned liposome dispersion. As a result, the percentage of doxorubicin, the active ingredient retained by liposomes, was almost 100% in liposomes of Examples 2, 4 and 5, and Control Examples 1 and 2 as shown in Table 1. Therefore, each original liposome dispersion was used without any treatment, and diluted 4/3 times with physiological saline for the experiment utilizing rats described below (thus, final medicament concentration: 1.5 mg/mL, final lipid concentration: 15 mM). Further, the liposomes of Examples 1 and 3, and Control Examples 3 and 4 were subjected to ultracentrifugation (65,000 rpm, 1 hour) to remove unencapsulated medicament in the supernatant and then reconstituted with physiological saline so that a final medicament concentration of 1.5 mg/mL was obtained (thus, final lipid concentrations were about 20.9 mM in Example 1, about 19.3 mM in Example 3, about 17.2 mM in Control Example 3, and about 18.7 mM in Control Example 4). The particle diameters of the liposomes were around 100 nm for all the examples.

(3) Experiment for Evaluation of Circulating in Blood in Rats

An experiment for evaluation of circulating in blood was performed in SD male rats (6-week old) using Examples 1 to 5 and Control Examples 1 to 4 mentioned above. Each liposome dispersion was administered to rats from the cervical vein under ether anesthesia (each group consisted of 5 animals, dose: 7.5 mg doxorubicinl/5 mL/kg), then blood was collected in heparin (0.5 to 1 mL) from the cervical vein under ether anesthesia at each blood collection time (2, 4, 8, 24, 48, 72, 120, 168 hours) and subjected to plasma skimming. Then, in a conventional manner, the blood was pretreated, and plasma medicament concentration was measured by HPLC. The AUC (0 to ∞) was calculated from the plasma medicament concentration obtained with each formulation of liposome dispersion according to the trapezoidal rule. As shown in Table 1, AUCs larger by 1 order or more were obtained with the liposome formulations containing the phospholipid derivatives of the present invention (Examples 1 to 5) compared with AUCs obtained with the liposomes of Control Example 1 not containing the lipid derivative of the present invention, the liposomes of Control Example 2 added only with the phospholipid portion (DSPE: distearoylphosphatidylethanolamine) of the lipid derivative of the present invention, and the liposomes of Control Examples 3 and 4 added with the polyglycerin lipid derivatives disclosed in Japanese Patent Unexamined Publication (KOKAI) No. 6-228012 and literature (International Journal of Pharmacology, Vol. 111, page 103, 1994), and thus clearly longer circulating in the blood was observed with the liposome formulations containing the phospholipid derivatives of the present invention.

For Control Examples 14 and 15, the polyglycerin lipid derivatives disclosed in Japanese Patent Unexamined Publication (KOKAI) No. 6-228012 and the literature (International Journal of Pharmacology, Vol. 111, pages 103, 1994) were used. formulations containing the phospholipid derivatives of the present invention.

TABLE 1

| | Liposome membrane composition | Particle size (nm) | Percentage of carried active ingredient (%) | $AUC_0$-$\infty$ ± S.D. (μg·hr/mL) |
|---|---|---|---|---|
| Example 1 | DSPE-PG(8)/HSPC/Cholesterol = 2.08 mM/11.28 mM/7.68 mM | 92 | 71.8 | 3417 ± 224 |
| Example 2 | DSPE-PG(40)/HSPC/Cholesterol = 0.72 mM/11.28 mM/7.68 mM | 76 | 100.0 | 3775 ± 1038 (n = 4) |
| Example 3 | DSPE-PG(6)Glu/HSPC/Cholesterol = 2.08 mM/11.28 mM/7.68 mM | 94 | 77.6 | 4264 ± 131 |
| Example 4 | DSPE-PG(8)Glu/HSPC/Cholesterol = 2.08 mM/11.28 mM/7.68 mM | 78 | 96.6 | 4284 ± 249 |
| Example 5 | DSPE-PG(10)Glu/HSPC/Cholesterol = 2.08 mM/11.28 mM/7.68 mM | 83 | 100.0 | 4034 ± 387 |
| Control Example 1 | HSPC/Cholesterol = 11.90 mM/8.10 mM | 91 | 100.0 | 452 ± 98 |
| Control Example 2 | DSPE/HSPC/Cholesterol = 1.04 mM/11.28 mM/7.68 mM | 94 | 100.0 | 397 ± 133 |
| Control Example 3 | DSPPG(4)/HSPC/Cholesterol = 1.04 mM/11.28 mM/7.68 mM | 125 | 87.4 | 317 ± 129 |
| Control Example 4 | DSPPG(6)/HSPC/Cholesterol = 1.04 mM/11.28 mM/7.68 mM | 146 | 80.4 | 233 ± 58 |

DSPE-PG(8): Synthesized in Example 4
DSPE-PG(40): Synthesized in Example 5
DSPE-PG(6)Glu: Synthesized in Example 1
DSPE-PG(8)Glu: Synthesized in Example 2
DSPE-PG(10)Glu: Synthesized in Example 3
HSPC: Hydrogenated soybean phosphatidylcholine
DSPPG(4) and DSPPG(6): Polyglycerin lipid derivatives disclosed in Japanese Patent Unexamined Publication No. 6-228012 and literature (Int. J. Pharm., 111, 103 (1994))

Example 7

Preparation of Skin Toner (Evaluation as Solubilizer)

A skin toner was prepared by using octaglycerol glutaryl distearoylphosphatidylethanolamine of Synthesis Example 4. Specifically, among the base materials in the composition shown in Table 2, glycerin and propylene glycol were added to purified water and uniformly dissolved. Other base materials were added to ethanol, and the mixture was made uniform, then added to the aforementioned purified water phase with stirring and solubilized to obtain a skin toner.

TABLE 2

| Propylene glycol | 5.0 wt % |
|---|---|
| Glycerin | 2.0 wt % |
| Oleyl alcohol | 0.5 wt % |
| Hydrogenated soybean lecithin | 0.5 wt % |
| Ethanol | 7.0 wt % |
| Octaglycerol glutaryl distearoylphosphatidylethanolamine | 2.0 wt % |
| Tocopherol | 0.02 wt % |
| Perfume | As required |
| Preservative | As required |
| Purified water | 73.0 wt % |

Example 8

Preparation of Liposome Emulsion (Evaluation as Dispersing Agent for Cosmetics)

Method for Preparing Liposomes

In an amount of 645 mg of hydrogenated soybean phosphatidylcholine, 299 mg of cholesterol, 23 mg of myristic acid (molar ratio: 1:1:0.1) and octaglycerol glutaryl distearoylphosphatidylethanolamine were added so that the mixed lipid concentration should become 5% by mole, added with 10 to 11 mL of physiological saline heated at 60° C. beforehand so that the mixed lipid concentration was 10% by mass and stirred, and further mixed by using a homogenizer on a water bath at 60° C. for 10 minutes to obtain a liposome solution. Among the base materials of the composition shown in Table 3, those of the oil phase containing an emulsifier were heated at 60° C. and uniformly dissolved, and those of the aqueous phase using the liposome solution were added at the same temperature with stirring to obtain a liposome emulsion.

TABLE 3

| Oil phase: | |
|---|---|
| Cetanol | 2.0 wt % |
| Vaseline | 2.0 wt % |
| Squalane | 5.0 wt % |
| Liquid paraffin | 10.0 wt % |
| Polyoxyethylene monooleic acid ester | 2.0 wt % |
| Tocopherol | 0.02 wt % |
| Perfume | As required |
| Preservative | As required |
| Aqueous phase: | |
| Propylene glycol | 2.0 wt % |
| Purified water | 67.0 wt % |
| Liposome solution | 10.0 wt % |

Comparative Synthesis Example 1

(1) Synthesis of Monomethylpolyoxyethylenecarbamyl (Molecular Weight: 2000) Distearoylphosphatidylethanolamine Monomethoxypolyoxyethylene (molecular weight: 2000, 20 g, 10 mmol) was added with toluene (80 mL), and then refluxed by raising a temperature up to 110° C. for dehydration. The reaction mixture was added with 1,1'-carbonyldiimidazole (1.95 g, 12 mmol) and reacted at 40° C. for 2 hours. The reaction mixture was added with pyridine (1.58 g, 20 mmol) and distearoylphosphatidylethanolamine (7 g, 9.36 mmol), and reacted at 65° C. for 5 hours. The reaction mixture was added with hexane (300 mL) for crystallization. The crystals were added with ethyl acetate (400 mL), dissolved at 65° C., stirred for 30 minutes, and then cooled to 5° C. The deposited crystals were collected by filtration. This procedure using ethyl acetate was repeated again in a similar manner. The crystals were dissolved in ethyl acetate (400 mL), added with Kyoward #700 (1 g) as an adsorbent, and stirred at 65° C. for 1 hour. The reaction mixture was filtered, and then cooled to 5° C. for crystallization. The crystals were washed with hexane (200 mL), collected by filtration, and dried to obtain 15.3 g (yield: 54.7%) of monomethylpolyoxyethylenecarbamyl distearoylphosphatidylethanolamine with a purity of 98.3%. The product was analyzed by thin layer chromatography (TLC) utilizing a silica gel plate. A mixed solvent of chloroform and methanol at a volume ratio of 85:15 was used as a developing solvent, and substances contained were identified and quantified by coloration with iodine vapor on the basis of comparison with standard substances of known amounts.

Example 9

Measurement of Salt-Tolerant Effect (Evaluation as Surfactant)

Clouding point of a 1 mass % solution of tetradecaglycerol succinyl distearoylphosphatidylethanolamine obtained in Example 5, which was dissolved in 5 mass % aqueous solution of sodium sulfate, was measured. As a result of the measurement, clouding point could not be detected even when the temperature was raised to 80° C.

Comparative Example 1

Comparison of Salt Salt-Tolerant Effect (Evaluation as Surfactant)

Clouding point was measured for monomethylpolyoxyethylenecarbamyl (molecular weight: 2000) distearoylphosphatidylethanolamine obtained in Comparative Synthesis Example 1 in the same manner as used in Example 9. As a result of the measurement, clouding point was found to be 50.0° C. Thus, it was revealed that the phospholipid derivative of the present invention exhibited high salt tolerance.

Example 10

Evaluation as Surfactant

Preparation of Polymer Micelle Solution of Hydrogenated Soybean Phosphatidylcholine Using Octaglycerol Glutaryl Distearoylphosphatidylethanolamine Distilled water (5 mL) was added with hydrogenated soybean phosphatidylcholine (0.1 g, 0.13 mmol) and octaglycerol glutaryl distearoylphosphatidylethanolamine (1 g, 0.17 mmol), and mixed by stirring. The resulting uniform mixed solution was gradually added with distilled water (95 mL) with stirring to obtain a transparent uniform polymer micelle solution. Particle size distribution in the obtained solution was measured by using a particle sizer (NICOMP Model 370, produced by Nozaki & Co., Ltd.). As a result, mean particle size was found to be 40 nm. The resulting polymer micelle solution was left for one month at room temperature. After 3 months, the polymer micelle solution had a condition of a uniform polymer micelle solution and gave no change under visual inspection and no precipitates.

Example 11

Synthesis of Octaglycerol Nonaglutarate (Compound of the Following Formula wherein k=8, k2=9, and k3=1)

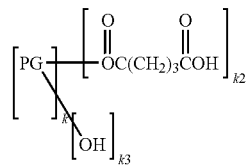

Octaglycerin (6.1 g, 0.01 mol) was dispersed in dimethyl sulfoxide (50 mL), added with 9.0 g (0.11 mol) of sodium acetate, warmed to 70° C., and then added with 11.4 g (0.1 mol) of glutaric anhydride and reacted for 12 hours. After completion of the reaction, sodium acetate was removed by filtration, and dimethyl sulfoxide was evaporated under reduced pressure by using an evaporator to obtain 15.9 g of octaglycerol nonaglutarate.

Acid value and hydroxyl value of the resulting compound were measured. The acid value was found to be 310.8, and hydroxyl value was 36.1. On the basis of these results, it was revealed that about 9 hydroxyl groups of octaglycerin were glutarated, and about one hydroxyl group existed. Thus the compound obtained was proved to be octaglycerol nonaglutarate.

By $^1$H-NMR (CDCl$_3$), protons of methyl group of —O(C=O)CH$_2$C$\underline{H}_2$CH$_2$COO— derived from glutaric acid at δ 1.97, protons of methylene group of —O(C=O)C$\underline{H}_2$CH$_2$C$\underline{H}_2$COO— at δ 2.41 and 2.44, methylene protons and methine protons derived from octaglycerin at δ 3.2-4.6 were observed.

Synthesis of Octaglycerol Heptaglutaryl Phosphatidylethanolamine Glutarate (Compound of the Following Formula wherein k=8, k1=1, k2=8, and k3=1)

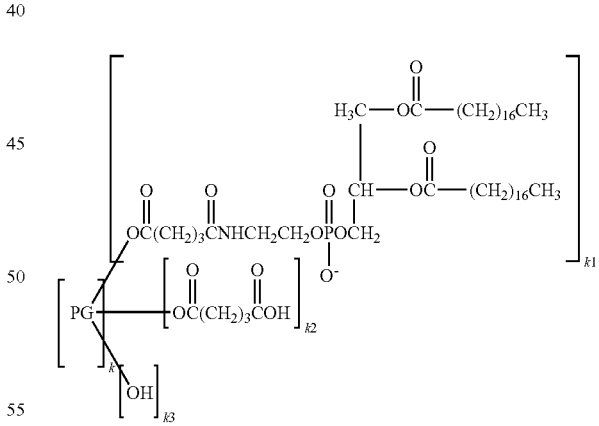

Distearoylphosphatidylethanolamine (9.4. g, 0.012 mmol) was added with chloroform (150 mL) and stirred at 45° C. This phospholipid/chloroform solution was added with 15.9 g (0.097 mol) of the aforementioned crude octaglycerol glutarate dissolved in dimethyl sulfoxide (15 mL), and then added with 2.4 g (0.012 mol) of dicyclohexylcarbodiimide, 1.3 g (0.012 mol) of triethylamine and 1.4 g (0.012 mol) of N-hydroxysuccinimide, and reacted for 3 hours.

Completion of the reaction was confirmed by TLC, specifically completion was confirmed by thin layer chromatography (TLC) utilizing a silica gel plate where no distearoylphosphatidylethanolamine was detected. As the developing solvent, a mixed solvent of chloroform, methanol and water at a volume ratio of 65:25:4 was used. After the completion of the reaction, the deposited dicyclohexylurea was removed by filtration, and then the filtrate was passed through a cation exchange resin (DIAION SK1BH) filled in a column. The eluate was received in aqueous disodium hydrogenphosphate added with a small amount of methanol for neutralization. The eluate was dehydrated over sodium sulfate, then filtered, and concentrated. The residue was crystallized 3 times from chloroform/acetone/dimethyl sulfoxide, or acetone/dimethyl sulfoxide to obtain 18.1 g of octaglycerol glutaryl distearoylphosphatidylethanolamine.

By $^1$H-NMR (CDCl$_3$), protons of methyl group at the end of the stearoyl group at δ 0.88, protons of methylene group of the stearoyl group at δ 1.26, protons of methylene group of —NH(C=O)CH$_2$CH$_2$CH$_2$COO— derived from glutaric acid at δ 1.95, protons of methylene group of —NH(C=O)C H$_2$CH$_2$CH$_2$COO— at δ 2.29 and 2.31, methylene protons and methine protons derived from octaglycerin at δ 3.2-4.5 were observed.

Example 12

(8) Preparation of Hexaglycerol Distearoylphosphatidylethanolamine Succinate Ester

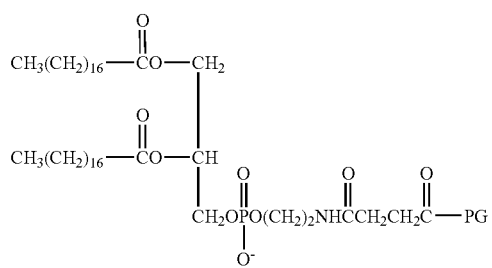

(6)

Distearoylphosphatidylethanolamine succinate (4.2 g, 5.0 mmol) was added with chloroform (10 mL) and stirred at 45° C. The chloroform solution was added with 11.6 g (25 mmol) of hexaglycerin dissolved in dimethyl sulfoxide (20 mL), and then added with 2.1 g (1.0 mmol) of dicyclohexylcarbodiimide and 0.64 g (5.3 mmol) of dimethylaminopyridine. The reaction was performed at 45° C. for 2 hours. Completion of the reaction was confirmed by TLC in the same manner as described above.

After the completion of the reaction, the deposited dicyclohexylurea was removed by filtration, and then the filtrate was passed through a cation exchange resin (DIAION SK1BH) filled in a column. The eluate was received in aqueous disodium hydrogenphosphate added with a small amount of methanol for neutralization.

The eluate was dehydrated over sodium sulfate, then filtered and concentrated. The residue was crystallized 3 times from chloroform/acetone/dimethyl sulfoxide, or acetone/dimethyl sulfoxide to obtain 4.7 g of crystals of hexaglycerol distearoylphosphatidylethanolamine succinate ester.

By $^1$H-NMR (CDCl$_3$), protons of methyl group at the end of the stearoyl group at δ 0.88, protons of methylene group of the stearoyl group at δ 1.26, protons of methylene group of —NH(C=O)CH$_2$CH$_2$COO— derived from succinic acid at δ 2.29 and 2.31, methylene protons and methine protons derived from hexaglycerin at δ 3.2-4.5 were observed.

(Evaluation as Solubilizer)

Cyclosporin A (25 mg, produced by Sigma) was weighed in a sample tube, and dissolved in dimethyl sulfoxide (1 mL) to prepare a cyclosporin A/dimethyl sulfoxide solution. The octaglycerol succinyl distearoylphosphatidylethanolamine (30 mg) obtained in Example 4 was added with 200 μL of the cyclosporin A/dimethyl sulfoxide solution obtained above, and completely dissolved by warming. The resulting solution was added with 800 μL of purified water, and sufficiently stirred.

In the same manner, experiment was also performed with the hexaglycerol distearoylphosphatidylethanolamine succinate ester obtained in Example 12.

Then, experiment was also performed similarly with medroxyprogesterone acetate (produced by Sigma).

Medroxyprogesterone acetate (2.5 mg) was weighed in a sample tube, and dissolved in DMSO (1 mL) to prepare a cyclosporin A/DMSO solution. The octaglycerol succinyl distearoylphosphatidylethanolamine (30 mg) obtained in Example 4 was added with 200 μL of the cyclosporin A/DMSO solution obtained above, and completely dissolved by warming. The solution obtained was added with 800 μL of purified water, and sufficiently stirred.

In the same manner, experiment was also performed with the hexaglycerol distearoylphosphatidylethanolamine succinate ester obtained in Example 12.

Complete solubilization was observed by visual inspection, and the results were indicated with ○ when complete dissolution was obtained, or with X when any insolubility was observed.

○: Transparent

X: Turbid

For Control Examples 14 and 15, the polyglycerin lipid derivatives disclosed in Japanese Patent Unexamined Publication (KOKAI) No. 6-228012 and the literature (International Journal of Pharmacology, Vol. 111, pages 103, 1994) were used.

For Control Example 16, Cremophor EL (polyoxyl 35 castor oil, produced by Sigma) was used.

All the results are shown in Table 4.

TABLE 4

|  |  | Cyclosporin A | Medroxy-progesterone acetate |
|---|---|---|---|
| Example 13 | DSPE-PG(6) | ○ | ○ |
| Example 14 | DSPE-PG(8) | ○ | ○ |
| Control Example 14 | DSPPG(6) | X | X |
| Control Example 15 | DSPPG(8) | X | X |
| Control Example 16 | Cremophor EL | X | X |

DSPE-PG(6): Synthesized in Example 12
DSPE-PG(8): Synthesized in Example 4
DSPPG(4) and DSPPG(6): Polyglycerin lipid derivatives disclosed in Japanese Patent Unexamined Publication No. 6-228012 and the literature (Int. J. Pharm., 111, 103 (1994))

INDUSTRIAL APPLICABILITY

The phospholipid derivative of the present invention is highly safe for living bodies and useful as a surfactant, solubilizer, or dispersing agent in the fields of cosmetics and the like. When the phospholipid derivative of the present invention, which is a polyglycerin derivative, is used for preparing a lipid membrane structure such as liposome, aggregation of microparticles in an aqueous medium is prevented without causing instability of the lipid membrane structure, and a stable solution state can be obtained. Further, a liposome containing the phospholipid derivative of the present invention is characterized to have a longer circulating time in blood.

What is claimed is:

1. A phospholipid derivative represented by the following formula (1):

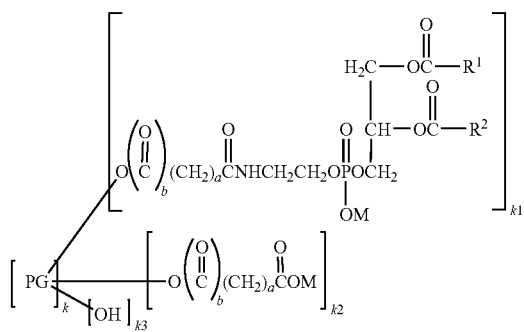

wherein [PG]k represents a residue of polyglycerin having a polymerization degree of k, wherein k is 2 to 50, $R^1CO$ and $R^2CO$ independently represent an acyl group having 8 to 22 carbon atoms, symbol "a" independently represents an integer of 0 to 5, symbol "b" independently represents 0 or 1, M represents hydrogen atom, an alkali metal atom, an ammonium, or an organic ammonium, and k1, k2, and k3 represent numbers satisfying the following conditions: $1 \leq k1 \leq (k+2)/2$, $0 \leq k2$, and $k1+k2+k3=k+2$.

2. The phospholipid derivative according to claim 1, wherein k1 satisfies $1 \leq k1 \leq 2$.

3. The phospholipid derivative according to claim 1, wherein k2 satisfies $0 \leq k2 \leq 1$.

4. The phospholipid derivative according to claim 1, wherein k1, k2, and k3 satisfy $8 \leq k1+k2+k3 \leq 52$.

5. The phospholipid derivative according to claim 1, wherein $R^1CO$ and $R^2CO$ independently represent an acyl group having 12 to 20 carbon atoms.

6. The phospholipid derivative according to claim 1, wherein k2 is 0.

7. The phospholipid derivative according to claim 6, wherein a and b represent 0.

8. The phospholipid derivative according to claim 1, wherein k2 satisfies $0<k2$.

9. A lipid membrane structure comprising the phospholipid derivative according to claim 1.

10. The lipid membrane structure according to claim 9, which is a liposome.

11. A surfactant comprising the phospholipid derivative according to claim 1.

12. A solubilizer comprising the phospholipid derivative according to claim 1.

13. A dispersing agent comprising the phospholipid derivative according to claim 1.

14. A method for producing the phospholipid derivative according to claim 1, which comprises reacting a compound represented by the following formula (2):

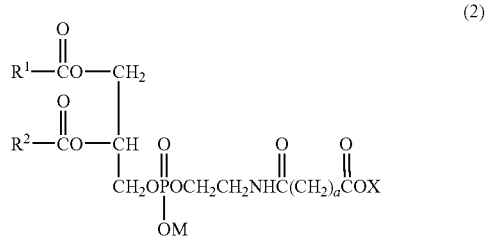

$R^1$, $R^2$, a, and M have the same meanings as defined above, and X represents hydrogen atom or N-hydroxysuccinimide, with a polyglycerin represented by the following formula (3):

wherein [PG]k represents a residue of polyglycerin having a polymerization degree of k, wherein k has the same meaning as defined above, and k4 is a number satisfying the following condition: $k4=k+2$.

15. A method for producing the phospholipid derivative according to claim 1, which comprises:

(A) reacting a polyglycerin with a dibasic acid or a halogenated carboxylic acid to obtain a carboxylated polyglycerin; and (B) reacting the carboxylated polyglycerin obtained in (A) with a phospholipid.

16. A method for producing the phospholipid derivative according to claim 1, which comprises:

(A) reacting a polyglycerin with a halogenated carboxylic acid ester and hydrolyzing the resulting ester compound to obtain a carboxylated polyglycerin; and (B) reacting the carboxylated polyglycerin obtained in (A) with a phospholipid.

17. A method for producing the phospholipid derivative according to claim 1, which comprises reacting a polyglycerin derivative represented by the following formula (4):

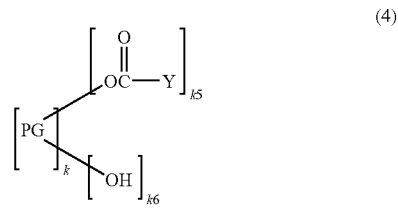

wherein [PG]k represents a residue of polyglycerin having a polymerization degree of k, wherein k represent a number of 2 to 50, Y represents hydroxyl group or a leaving group, and k5 and k6 are numbers satisfying the following conditions: $1 \leq k5 \leq (k+2)/2$, and $k5+k6=k+2$, with a phospholipid represented by the following formula (5):

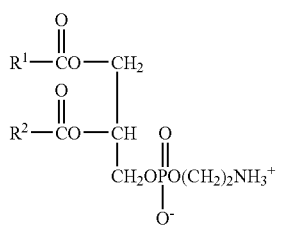
(5)
wherein $R^1$ and $R^2$ have the same meanings as defined above, in an organic solvent in the presence of a basic catalyst.
18. A pharmaceutical composition containing the lipid membrane structure according to claim 9 retaining a medicament.
19. The pharmaceutical composition according to claim 18, wherein the medicament is an antitumor agent.
* * * * *

UNITED STATES PATENT AND TRADEMARK OFFICE
CERTIFICATE OF CORRECTION

| | | |
|---|---|---|
| PATENT NO. | : 7,524,981 B2 | Page 1 of 1 |
| APPLICATION NO. | : 10/541309 | |
| DATED | : April 28, 2009 | |
| INVENTOR(S) | : Kubo et al. | |

It is certified that error appears in the above-identified patent and that said Letters Patent is hereby corrected as shown below:

At column 32, line 4 (claim 14, line 4) of the printed patent, please insert -- wherein -- before "$R^1$".

Signed and Sealed this

Eighth Day of December, 2009

David J. Kappos
*Director of the United States Patent and Trademark Office*